US012755824B2

(12) United States Patent
Eetemadi et al.

(10) Patent No.: US 12,755,824 B2
(45) Date of Patent: Oct. 6, 2026

(54) FRAMEWORK FOR CONSTRAINED ADAPTIVE GROUP TESTING

(71) Applicant: The Regents of the University of California, Oakland, CA (US)

(72) Inventors: Ameen Eetemadi, Davis, CA (US); Ilias Tagkopoulos, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/715,605

(22) PCT Filed: Dec. 29, 2022

(86) PCT No.: PCT/US2022/054278
§ 371 (c)(1),
(2) Date: May 31, 2024

(87) PCT Pub. No.: WO2023/129672
PCT Pub. Date: Jul. 6, 2023

(65) Prior Publication Data

US 2025/0046415 A1 Feb. 6, 2025

Related U.S. Application Data

(60) Provisional application No. 63/295,295, filed on Dec. 30, 2021.

(51) Int. Cl.
*G16H 20/00* (2018.01)
*G16H 50/20* (2018.01)

(52) U.S. Cl.
CPC ............ *G16H 20/00* (2018.01); *G16H 50/20* (2018.01)

(58) Field of Classification Search
None
See application file for complete search history.

(56) References Cited

U.S. PATENT DOCUMENTS 10,586,622 B2 3/2020 Livesay et al.
11,244,752 B2 * 2/2022 Grimmer ............ G06F 16/9535
(Continued)

FOREIGN PATENT DOCUMENTS

WO 2014/055718 A1 4/2014
WO 2015/095343 A1 6/2015
(Continued)

OTHER PUBLICATIONS

Olah, P., et al. "A Database Design Pattern for Structuring Hierarchical Medical Data." Acta Medica Marisiensis 58.6 (2012). (Year: 2012).*

(Continued)

*Primary Examiner* — Constantine Siozopoulos
(74) *Attorney, Agent, or Firm* — Kilpatrick Townsend & Stockton LLP

(57) ABSTRACT

Described herein is a system and method for determining potency of lifestyle interventions. For a set of lifestyle interventions (LIs), a potency probability is estimated for each LI. A catalog is generated to include data associated with the set of LIs. The set of LIs is partitioned into a plurality of disjoint sets of LIs based on the catalog and the estimated potency probabilities. For each disjoint set, a model is applied to determine a potency of each LI such that an optimum number of rounds are utilized in determining potency of each LI included in the set. The set of LIs and their computed potencies are rendered in a graphical user interface displayed on a user's device.

20 Claims, 19 Drawing Sheets

(56) References Cited

U.S. PATENT DOCUMENTS

| | | | |
|---|---|---|---|
| 2008/0147438 A1 | 6/2008 | Kil | |
| 2008/0228735 A1 | 9/2008 | Kenedy et al. | |
| 2011/0184944 A1 | 7/2011 | Kenedy et al. | |
| 2017/0032694 A1 | 2/2017 | Brueckner et al. | |
| 2019/0074080 A1 | 3/2019 | Appelbaum et al. | |
| 2023/0051283 A1* | 2/2023 | Nicolaas | G16H 15/00 |

FOREIGN PATENT DOCUMENTS

| | | | |
|---|---|---|---|
| WO | 2019/173629 A1 | 9/2019 | |
| WO | WO-2019183404 A1 * | 9/2019 | G16H 20/60 |

OTHER PUBLICATIONS

International Search Report and Written Opinion from International Appln. PCT/US2022/054278 mailed Apr. 12, 2023; 7 pages.
International Search Report and Written Opinion from International Appln. PCT/US2022/054254 mailed May 5, 2023; 8 pages.
Eetemadi, A.; "Computational Method for Optimization of Biological Organisms"; UC Davis Proquest; Dissertation; Chapter 5, Appendix A; https://escholarship.org/uc/item/0qz2s2s9.; Nov. 5, 2021; 152 pages.
Eetemadi, A. et al.; "Algorithmic lifestyle optimization"; Journal of the American Medical Informatics Association; Sep. 29, 2022; 8 pages.
U.S. Appl. No. 18/713,420, Final Office Action, mailed Mar. 12, 2026, 9 pages. U.S. Patent & Trademark Office, Alexandria, Virginia.

* cited by examiner

THE CAGT CATALOG * FOR
PERFORMING LOOKUPS

*|g|* : # OF LIS IN g
*l* : MIN # OF POTENT LIS
*h* : MAX # OF POTENT LIS
*s* : OPTIMAL ROUND SIZE
*w* : MAX # OF ROUNDS

*: THE CATALOG IS BUILT
BEFOREHAND AND CAN SERVE
ALL THE LOOKUPS NEEDED IN
CAGT.

1110

1120

1130

FRAMEWORK FOR CONSTRAINED ADAPTIVE GROUP TESTING

CROSS-REFERENCES TO RELATED APPLICATIONS

This application is a non-provisional of and claims the benefit of the filing date of U.S. Provisional Application No. 63/295,295, filed on Dec. 30, 2022, the contents of which are incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. 2020-67021-32855, awarded by the US Dept. of Agriculture and Grant No. 1743101 awarded by the National Science Foundation. The Government has certain rights in the invention.

FIELD

The present disclosure relates generally to a framework for rapid identification of effective lifestyle interventions.

BACKGROUND

A hallmark of personalized medicine and nutrition is to identify effective treatment plans at the individual level. Lifestyle interventions, from diet to exercise, can have a significant effect over time, especially in the case of chronic conditions. Due to the large combinatorial search space, it is difficult to test and evaluate which intervention plan would be more favorable for any given individual.

The variance of responses to lifestyle interventions (LIs) has been a major challenge in the fields of nutrition and medicine. Typical LIs include changes in diet, exercise, administrating drugs, stress management, smoking cessation, assisted sleep methods, and fasting, among others. Further, biomarkers can be used to predict an individual's response to a given lifestyle intervention. However, such biomarkers are often difficult to acquire and carry limited information when in isolation. Therefore, trial-and-error remains as the main alternative in which target health metrics are evaluated following an LI regimen to determine an individual's response.

Previous studies have proposed and measured the adoption of systematic strategies for particular interventions including diet and physical activity. The standard elimination diet (SED) is used for identification of food allergies in serous otitis, atopic dermatitis (eczema), as well as food intolerances in irritable bowel syndrome (IBS), esophagitis, and ADHD among others. In SED, series of oral food challenges are used in which target symptoms are evaluated following dietary elimination and subsequent introduction of each food for 2-3 days at a time. More recently, N-of-1 trials have emerged for systematic personalization of medical treatments in cases were the individualized potency of alternative treatment strategies need to be determined. They involve trial periods during which alternative treatments are followed one after the other and treatment outcomes are measured in order identify the treatment with the best statistical support.

N-of-1 trials are used for dietary intervention in inflammatory bowel disease, determining the impact of dietary macronutrients on postprandial glucose response, and personalized goal setting strategies to increase physical activity among others. These trial-and-error approaches commonly involve a single LI at a time, which is impractical and sub-optimal when there is a large number of non-interacting candidate Us. Therefore, the number of candidate Us that can be evaluated by an individual will be limited given the time that they can spend for determining LI responses.

Embodiments discussed herein address these and other issues individually as well as collectively.

SUMMARY

Embodiments of the present disclosure provide for a server (referred to herein as an Algorithmic Lifestyle Optimization (ALO) server) that is configured for rapid identification of effective lifestyle interventions. In its core, a group testing algorithm identifies the effectiveness of each intervention efficiently, within the context of its pertinent group. Evaluation on synthetic and real data in irritable bowel syndrome (IBS) food intolerances and allergic reactions show that ALO is robust to noise, data size, and data heterogeneity. When compared to standard of practice techniques, such as the standard elimination diet, ALO identifies the effective life interventions 58.9% to 68.4% faster. ALO provides for an approach for rapid discovery of effective interventions in nutrition and medicine that can lead to better intervention plans faster and with less inconvenience to the patient.

To address the issues of scalability, ALO provides for a systematic approach for identifying the individualized binary labels (i.e., potent or impotent) of the candidate Us, based on heterogeneous data, including biomarker information. In ALO, the required time for discovering candidate LI potencies in an individual is minimized using a group testing strategy. In its core, ALO uses an adaptive group testing strategy and involves multiple rounds of Us for each individual. In each round, a set of Us are provided to the individual to follow. These Us are chosen by ALO based on (a) the individual's health score (0|1) in response to each set of Us in prior rounds, and (b) the probability of a positive health score for each LI in a population. These probabilities may also be calibrated based on a biomarker when available. Further, ALO identifies the individual's response to each LI in minimal number of rounds and provides guarantees for both average and worst-case scenarios.

An aspect of the present disclosure provides for a method for group testing a set of lifestyle interventions. The method includes: initializing, by a server, a model with respect to a set of lifestyle interventions received from a device associated with a user, the initializing including: (i) representing the model as a tree including a plurality of nodes, wherein each node of the tree is representative of a list of lifestyle interventions and includes metadata information associated with the node, and (ii) assigning the set of lifestyle interventions received from the device to the list of lifestyle interventions associated with a root node of the tree; for each node of the tree: identifying, a first subset of the list of lifestyle interventions associated with the node to be assigned to a first child node of the node, and a second subset of the list of lifestyle interventions associated with the node to be assigned to a second child node of the node; selecting one of the first child node and the second child node to be utilized for a next round of processing based on an evaluation of each of the first child node and the second child node, updating metadata information associated with the first child node and the second child node based on the evaluation; and iteratively repeating the identifying, the selecting, and the updating until a stopping criterion is satisfied; and transmitting metadata information to be rendered in a user-interface displayed on the device associated with the user.

Another aspect of the present disclosure provides for a server for group testing a set of lifestyle interventions, the server comprising: a processor; and a memory including instructions that, when executed with the processor, cause the server to, at least: initialize a model with respect to a set of lifestyle interventions received from a device associated with a user, wherein initializing the model includes: (i) representing the model as a tree including a plurality of nodes, wherein each node of the tree is representative of a list of lifestyle interventions and includes metadata information associated with the node, and (ii) assigning the set of lifestyle interventions received from the device to the list of lifestyle interventions associated with a root node of the tree; for each node of the tree: (a) identify, a first subset of the list of lifestyle interventions associated with the node to be assigned to a first child node of the node, and a second subset of the list of lifestyle interventions associated with the node to be assigned to a second child node of the node; (b) select one of the first child node and the second child node to be utilized for a next round of processing based on an evaluation of each of the first child node and the second child node, (c) update metadata information associated with the first child node and the second child node based on the evaluation; and (d) iteratively repeat (a)-(c) until a stopping criterion is satisfied; and transmit metadata information to be rendered in a user-interface displayed on the device associated with the user.

One aspect of the present disclosure provides for non-transitory computer readable medium storing specific computer-executable instructions that, when executed by a processor, cause a computer system for performing group testing of a set of lifestyle interventions, the computer system configured to at least: initializing, by a server, a model with respect to a set of lifestyle interventions received from a device associated with a user, the initializing including: (i) representing the model as a tree including a plurality of nodes, wherein each node of the tree is representative of a list of lifestyle interventions and includes metadata information associated with the node, and (ii) assigning the set of lifestyle interventions received from the device to the list of lifestyle interventions associated with a root node of the tree; for each node of the tree, identifying, a first subset of the list of lifestyle interventions associated with the node to be assigned to a first child node of the node, and a second subset of the list of lifestyle interventions associated with the node to be assigned to a second child node of the node; selecting one of the first child node and the second child node to be utilized for a next round of processing based on an evaluation of each of the first child node and the second child node, updating metadata information associated with the first child node and the second child node based on the evaluation; and iteratively repeating the identifying, the selecting, and the updating until a stopping criterion is satisfied; and transmitting metadata information to be rendered in a user-interface displayed on the device associated with the user.

The foregoing, together with other features and embodiments will become more apparent upon referring to the following specification, claims, and accompanying drawings.

BRIEF DESCRIPTION OF THE DRAWINGS

Features, embodiments, and advantages of the present disclosure are better understood when the following Detailed Description is read with reference to the accompanying drawings.

DETAILED DESCRIPTION

In the following description, for the purposes of explanation, specific details are set forth in order to provide a thorough understanding of certain embodiments. However, it will be apparent that various embodiments may be practiced without these specific details. The figures and description are not intended to be restrictive. The word "exemplary"

is used herein to mean "serving as an example, instance, or illustration." Any embodiment or design described herein as "exemplary" is not necessarily to be construed as preferred or advantageous over other embodiments or designs.

Figure 1:
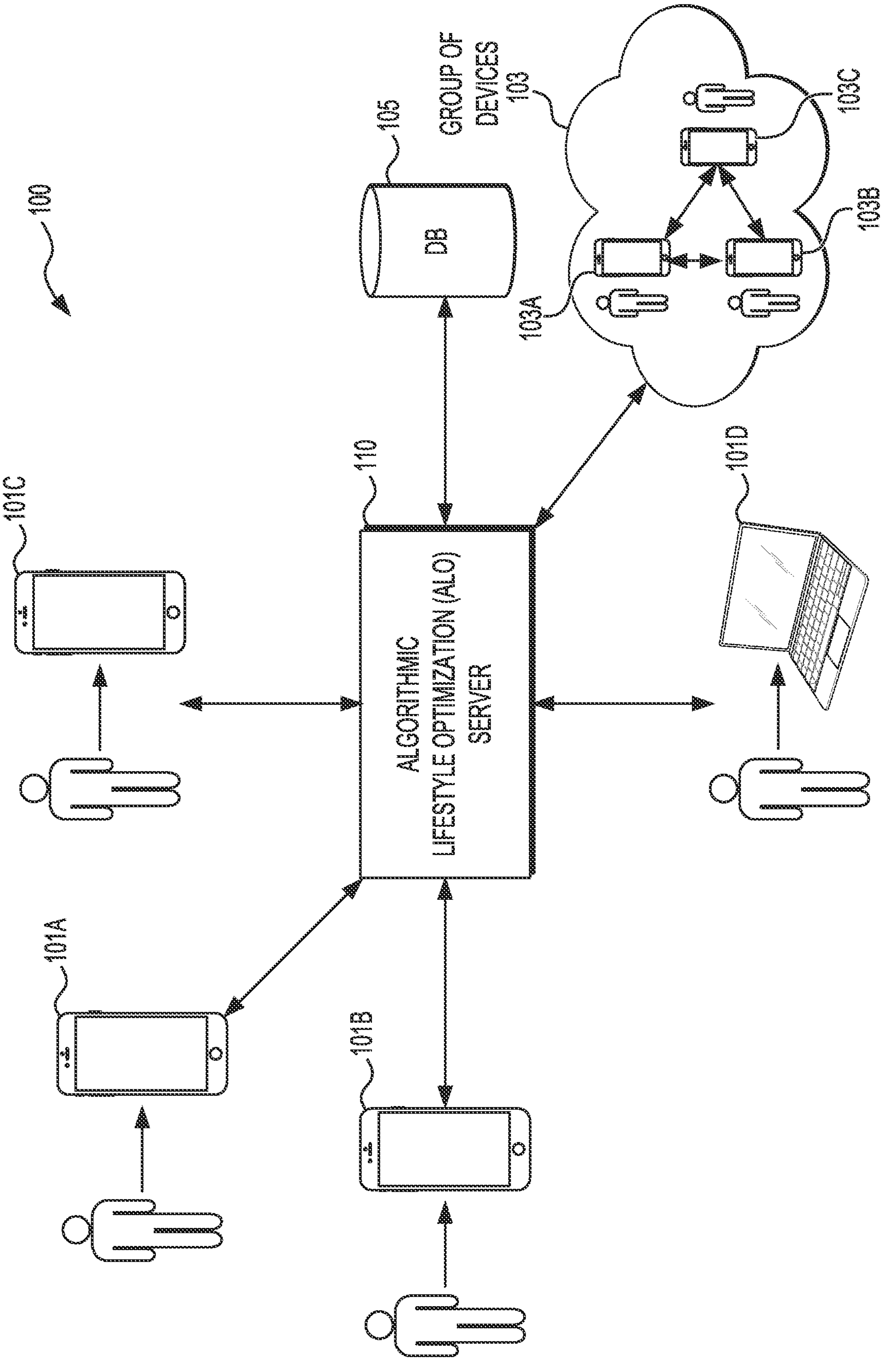
FIG. 1 depicts an exemplary high-level system diagram of an algorithmic lifestyle optimization (ALO) server, in accordance with various embodiments.

FIG. 1 depicts an exemplary high-level system diagram of an algorithmic lifestyle optimization (ALO) server, in accordance with various embodiments. As shown in FIG. 1, the system 100 includes a plurality of communication devices 101A, 101B, 101C, 111D, 103A-C, each of which is operated by a corresponding user. The communication devices may comprise any suitable electronic device that may be transported and operated by a user and may also provide remote communication capabilities to a network. Examples of communication devices include mobile phones (e.g., cellular phones), PDAs, tablet computers, net books, laptop computers, wearable devices (e.g., watches), personal music players, hand-held specialized readers, etc. A communication device may comprise any suitable hardware and software for performing such functions and may also include multiple devices or components (e.g., when a device has remote access to a network by tethering to another device—i.e., using the other device as a modem—both devices taken together may be considered a single mobile communication device). Each of the communication devices is communicatively coupled to an algorithmic lifestyle optimization (ALO) server 110. The ALO server 110 may be coupled to a backend database 105.

Each user may communicate with the ALO server 110 for rapid identification of effective lifestyle interventions (LIs). For instance, in one implementation, a user of the communication device may install an application on the device, wherein the user may select a group of LIs (e.g., candidate set of LIs) in the application. Such a candidate set of LIs may be transmitted from the communication device to the ALO server 110, in order to obtain a potency of each LI in the candidate set of LIs. In other words, ALO server 110 is configured to guide individuals in rapid discovery of LIs that are effective (i.e., potent) for them amongst many candidate LIs, for achieving a target health outcome.

The ALO server 110 upon determining a potency of each LI in the candidate set of LIs may transmit the potencies of the LIs to be rendered in a user interface (e.g., an interface of the application downloaded on the device) on the communication device operated by the user. Additionally, in some embodiments, the ALO server 110 may store the determined potencies of the candidate set of LIs (for each user) in a backend database 105. As such, the ALO server 110 may retrieve potencies of the candidate set of LIs from the database 105 to be provided to the user at a later time.

In some embodiments, a set of users may form a group 103 e.g., a group formed by communication devices 103A, 103B, and 103C. Each of the users of the group 103 may individually communicate with the ALO server 110 to obtain potencies of their respective LIs. Upon each user obtaining their respective potencies (corresponding to LIs selected by the user) from the ALO server 110, the user (e.g., user associated with communication device 103A) may transmit the results to other users in the group 103. In a similar manner, the user associated with communication device 103A may obtain results from other users in the group 103. Doing so, provides the user the flexibility to determine whether a particular LI chosen by another user may be selected by the user to achieve a target health outcome. It is appreciated that a particular user may select an LI chosen by another user based on several conditions/criteria such as similarity in health condition of the users, age of the users, medications currently being consumed by the users etc. It is appreciated that the communication between two devices in the group may occur via an electronic messaging option included in the downloaded application, wherein a user may transmit (to another user in the group), an electronic message including a web link that provides access to the set of LIs (and their associated potencies) associated with the user.

According to some embodiments, the ALO server 110, upon receiving the candidate set of Us from a device operated by a user, implements a model (referred to herein as algorithmic lifestyle optimization (ALO) model) to determine a potency of each LI included in the candidate set in a minimum number of rounds of intervention. The ALO model has three major modules, all of which rely on a constrained adaptive group testing (CAGT) framework (described later with reference to FIG. 5). In adaptive group testing, groups of available objects are selected in sequential rounds for testing, with the goal of determining, for instance, a potency of all the objects in a minimum number of rounds/iterations of the testing. It is appreciated that the group testing framework is applicable in cases where objects are non-interacting. This means that if multiple objects are tested together in a group, a positive test result is indicative of one or more objects being potent, while a negative test result indicates that the group is void of any potent objects.

Further, according to some embodiments, the ALO model is applicable in cases where (a) the individual is concerned about a single binary target health score such as having a symptom-free digestive state (0|1), (b) each LI is binary such as drinking coffee in the morning (yes/no), (c) it takes the same amount of time (e.g. 3-days) to see the impact of each LI on health score, (d) multiple LIs are independent hence can be followed together simultaneously, and (e) multiple LIs are non-interacting. Non-interacting LIs means that if a set of LIs together are determined to be "impotent" (i.e., not leading to a positive health score), one can conclude that each LI is also "impotent". However, when a given LI is "potent" (i.e., leading to a positive health score), it will remain as "potent" when combined with other LIs.

Figure 2:
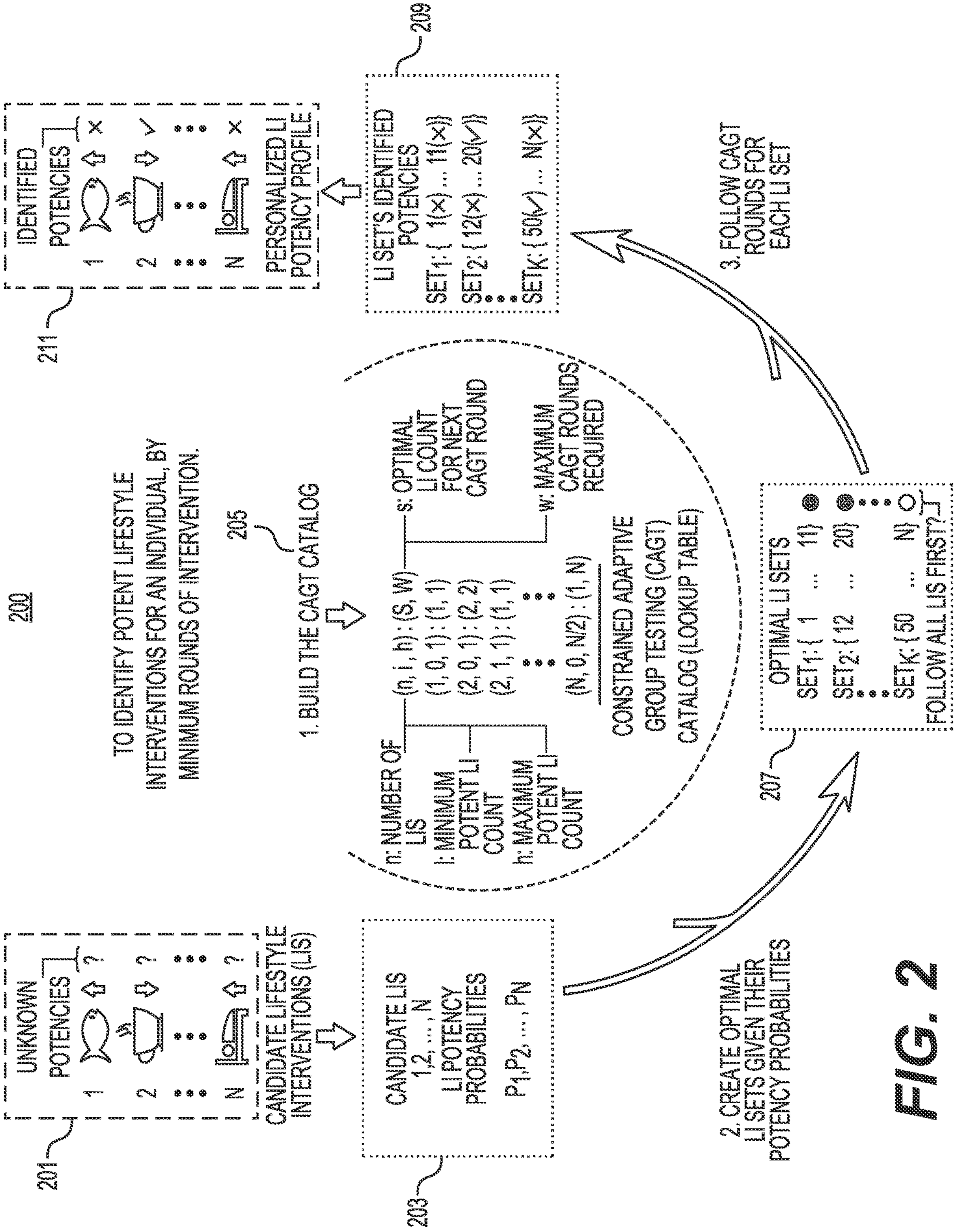
FIG. 2 depicts an exemplary operation of the ALO server, in accordance with various embodiments.

FIG. 2 depicts an exemplary operation performed by the ALO server, in accordance with various embodiments. Specifically, FIG. 2 depicts steps performed by the ALO model (implemented by the ALO server 110 of FIG. 1). The ALO model is designed to guide individuals in rapid discovery of lifestyle interventions (LIs) that are effective (potent) for them amongst many candidate LIs, for achieving a target health outcome. The ALO server receives as input a candidate set of LIs 201 having unknown potencies. For example, as shown in FIG. 2, the candidate set of LIs includes N lifestyle interventions, where a potency of each lifestyle intervention is unknown. Further, the ALO server estimates a potency probability for each lifestyle intervention included in the candidate set of lifestyle interventions. As shown in FIG. 2, the ALO server estimates probabilities (p1, p2, p3, . . . , pN) 203, corresponding to the N candidate set of lifestyle interventions. According to some embodiments, the potency probability for a lifestyle intervention in the set of lifestyle interventions is estimated based on a known potency of the lifestyle intervention with respect to a predetermined population of users.

According to some embodiments, the ALO model implements a constrained adaptive group testing (CAGT) algorithm in determining the potencies of the LIs included in the candidate set of LIs. The ALO model builds a CAGT catalog, which is a lookup table for finding the maximum number of rounds needed by the CAGT algorithm for identifying between l and h number of potent LIs amongst n candidate LIs. As shown in FIG. 2, the catalog includes a plurality of records, where record includes a mapping of a 3-tuple including parameters {n, l, h}, to a 2-tuple including parameters {s, w}. The parameter n corresponds to a number of lifestyle interventions, l corresponds to a minimum number of potent lifestyle interventions, h corresponds to a maximum number of potent lifestyle interventions, s corresponds to an optimal count of lifestyle interventions to be considered for execution of the model, and w corresponds to a maximum number of executions of the model that is required to obtain potencies of n lifestyle interventions.

Further, the ALO model implemented by the ALO server partitions the candidate set of LIs 201 into disjoint sets based on the potency probability of each LI that is determined based on the predetermined population of users. As shown in FIG. 2, optimal LI sets 207 are created by the partitioning of the candidate set of LIs 201. It is appreciated that the partitioning of the candidate set of LIs 201 into disjoint optimal sets 207 is performed so that the ALO model incurs the least number of rounds of execution to determine a potency for each LI included in the candidate set 201. Upon performing the partitioning of the candidate set of LIs into the optimal disjoint sets of LIs, 207, the ALO model executes sequentially, the CAGT algorithm with respect to each optimal set. It is noted that the CAGT algorithm is executed until a stopping criterion is satisfies e.g., stop once the potency of the LIs in each set is identified. Upon determining the potencies of each LI in the disjoint set of LIs 209, the ALO server can transmit the potencies of the candidate set of LIs 211 to be rendered in a user interface (UI).

According to some embodiments, the ALO model relies on the CAGT algorithm that aims to identify the minimal number of adaptive group testing rounds needed to identify the set of potent LIs ($V_1$) amongst the set of candidate LIs for a given individual, by solving the optimization problem:

$$R^* = \underset{R}{\operatorname{argmin}}|R| \tag{1}$$

$$\text{subject to } R = [R_1 \ldots R_{|R|}],\ R_i \subseteq LI,\ i = 1, \ldots, |R|$$

$$r = [r_1 \ldots r_{|R|}],\ r_i \in \{0, 1\},\ i = 1, \ldots, |R|$$

$$[V_0, V_1] = f(LI, R, r, l, h)$$

$$V_0 \cup V_1 = LI$$

$$l \le |V_1| \le h$$

In the above stated optimization problem, Ri⊆LI represents the group of Us that will be followed simultaneously by the individual in round i during which the potency of Ri will be determined as represented by ri∈{0: impotent, 1: potent}. V1 and V0 represent the sets of potent Us and impotent Us respectively which can be fully identified by a function $f$ given LI, R, r as well as the l:low and h:high bounds for the number of potent Us. The ALO model attempts to solve the optimization problem of equation (1) by utilizing three steps in each round, using the CAGT algorithm that captures l and h bounds for subsets of Us that are generated in each round. In step 1, a non-nested subset of Us (Ri) that is expected to minimize the final RI is identified. In step 2, the potency ri of Ri is determined by the individual based on their health score after following Ri. In step 3, the model is updated (given Ri and ri), and the sets of impotent and potent Us (V0 and V1) that can be determined using the updated model are identified. These three steps are repeated until the potency of all Us are identified.

Details of the individual steps utilized by the model e.g., building the CAGT catalog, partitioning the candidate set of Us, etc., are described next in detail with reference to FIG. 4A to FIG. 8.

Figure 3:
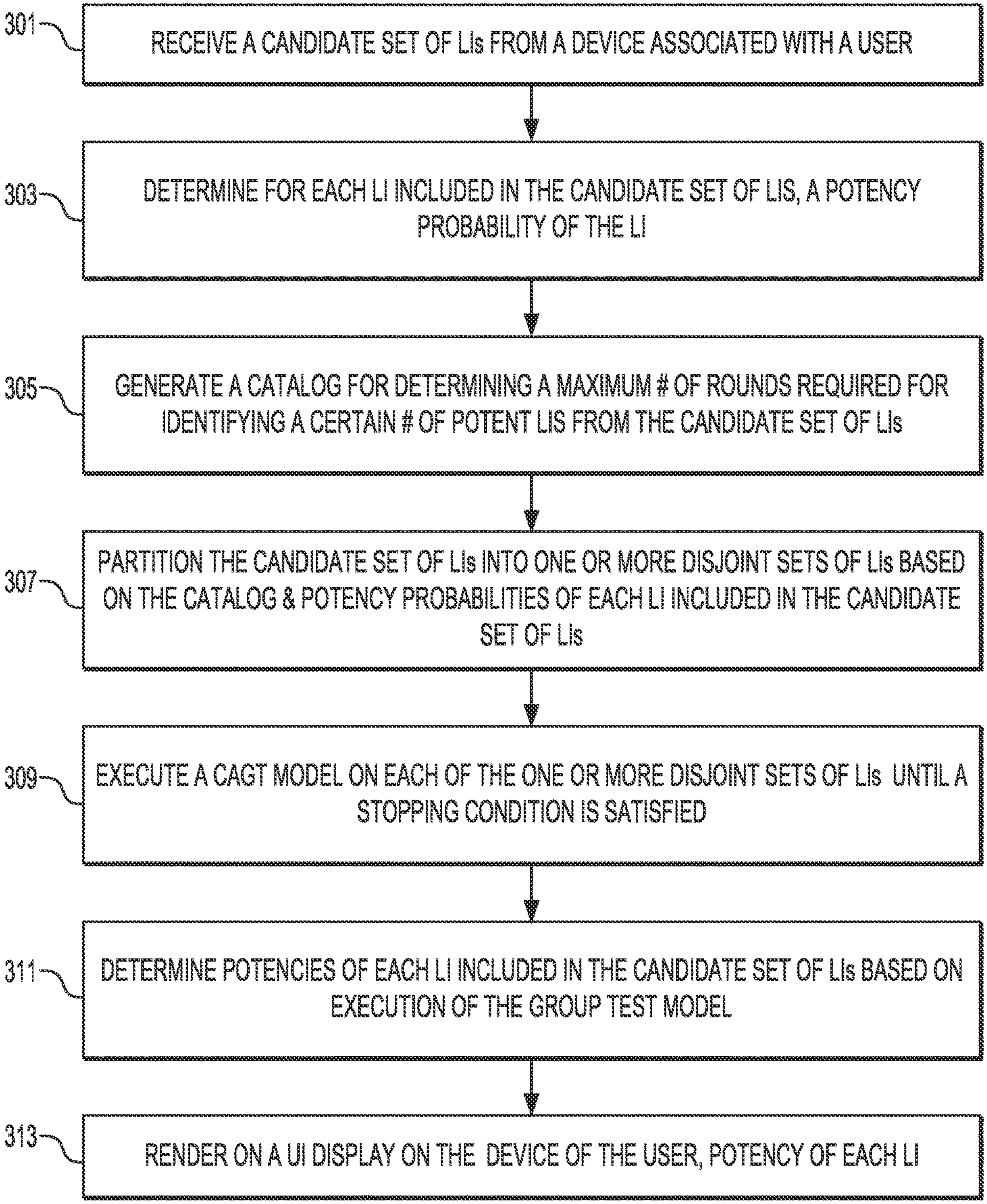
FIG. 3 depicts an exemplary flow diagram illustrating a process performed by the ALO server, in accordance with various embodiments.

FIG. 3 depicts an exemplary flow diagram illustrating a process performed by the ALO server, in accordance with various embodiments. The processing depicted in FIG. 3 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 3 and described below is intended to be illustrative and non-limiting. Although FIG. 3 depicts the various processing steps occurring in a particular sequence or order, this is not intended to be limiting. In certain alternative embodiments, the steps may be performed in some different order or some steps may also be performed in parallel.

The process commences in step 301, where the ALO server receives a candidate set of LIs from a device associated with a user. It is noted that the set of lifestyle interventions correspond to improving a health condition of the user. In step 303, for each LI included in the candidate set of LIs, the ALO server estimates a potency probability. For instance, the ALO server may estimate the potency probability based on a known potency of the lifestyle intervention with respect to a predetermined population of users.

The process in step 305 generates a catalog including data associated with the set of lifestyle interventions (i.e., the candidate set of LIs). In some implementations, the catalog includes a plurality of records, where each record includes metadata e.g., a mapping of a 3-tuple including parameters {n, l, h} to a 2-tuple including parameters {s, w}. The parameters are defined as follows: n corresponds to a number of lifestyle interventions, l corresponds to a minimum number of potent lifestyle interventions, h corresponds to a maximum number of potent lifestyle interventions, s corresponds to an optimal count of lifestyle interventions to be considered for execution of the model, and w corresponds to a maximum number of executions of the model that is required to obtain potencies of n lifestyle interventions. It is appreciated that the catalog aids in identifying a maximum number of rounds (i.e., parameter w) required for determining a certain number of potent LIs from the candidate set of LIs.

In step 307, the process partitions the set of lifestyle interventions (i.e., the candidate set of LIs) into a plurality of disjoint sets of lifestyle interventions based on the catalog and potency probabilities (determined in step 303) associated with the set of lifestyle interventions. For instance, as shown in FIG. 2, the ALO server partitions the candidate set of LIs 201 into the optimal disjoint LI sets (Set 1, Set 2, . . . Set N) 207. It is appreciated that the partitioning step is performed to minimize a total number of rounds of executing the model to obtain the potency of each lifestyle intervention in the set of lifestyle interventions.

Figure 4A:
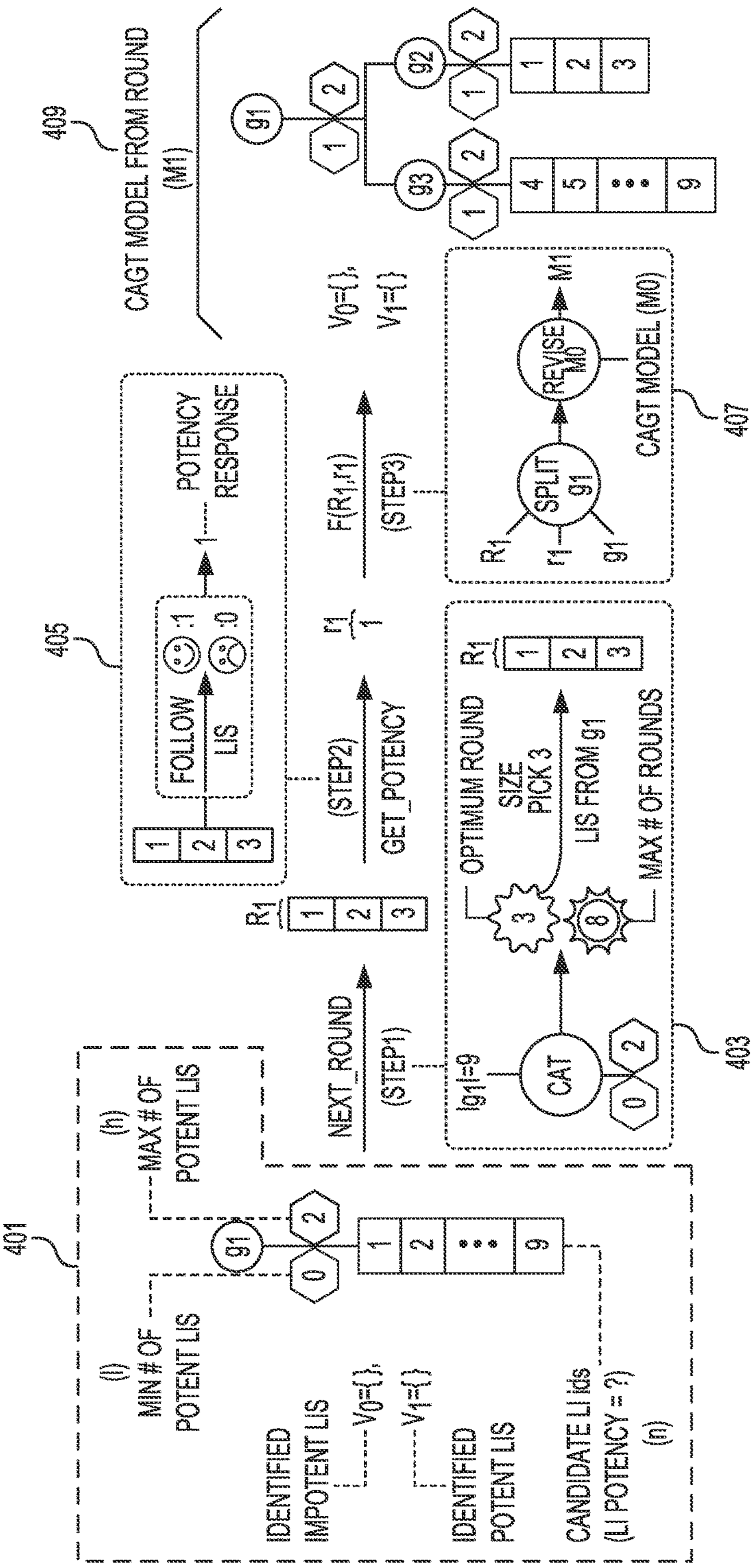
FIGS. 4A-4C illustrate exemplary steps performed by a constrained adaptive group testing (CAGT) algorithm employed by the ALO server, in accordance with various embodiments.

Upon partitioning the candidate set of LIs into the disjoint LI sets, the process in step 309, executes a model (i.e., CAGT model described later with reference to FIG. 5) on each set included in the disjoint LI sets. It is noted that the model applied for an optimum number of rounds for each disjoint set that is determined based on the catalog. It is appreciated that the optimum number of rounds required to determine the potency of each lifestyle intervention included in the disjoint set may be determined as follows: (i) identify a first record in the catalog corresponding to metadata associated with the disjoint set (e.g., parameters n, l, and h), and (ii) assigning a value of parameter w associated with the first record to correspond to the optimum number of rounds. It is appreciated that in the execution of each disjoint set by a constrained adaptive group testing (CAGT) model (as described next with reference to FIG. 5), a user provides a response (0/1) i.e., potency response 405 as shown in FIG. 4A, back to the server for a provided LI set.

The process thereafter proceeds to step 311, where a potency of each LI included in the candidate set of LIs is determined based on the iterative evaluation performed in step 309. According to some embodiments, a potency of each lifestyle intervention is a binary variable, wherein a potency value of '1' corresponds to the lifestyle intervention being potent, and the potency value of '0' corresponds to the lifestyle intervention being impotent. In step 313, the ALO server transmits the candidate set of Us, including a potency value for each LI, to the device operated by the user. In some implementations, the candidate set of Us along with the potency values determined by the ALO server may be rendered in user interface displayed on the device.

Figure 4B:
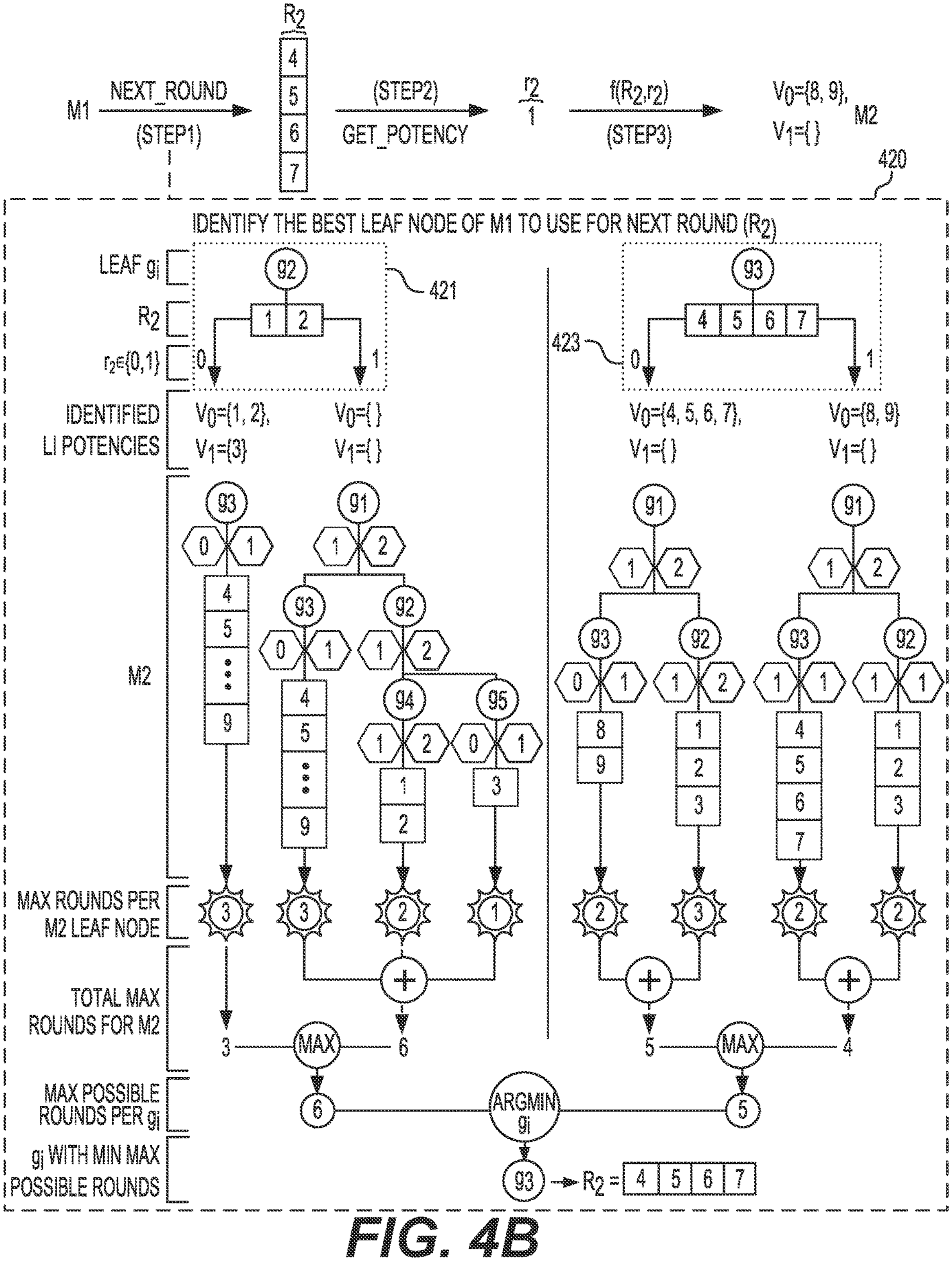
Figure 4C:
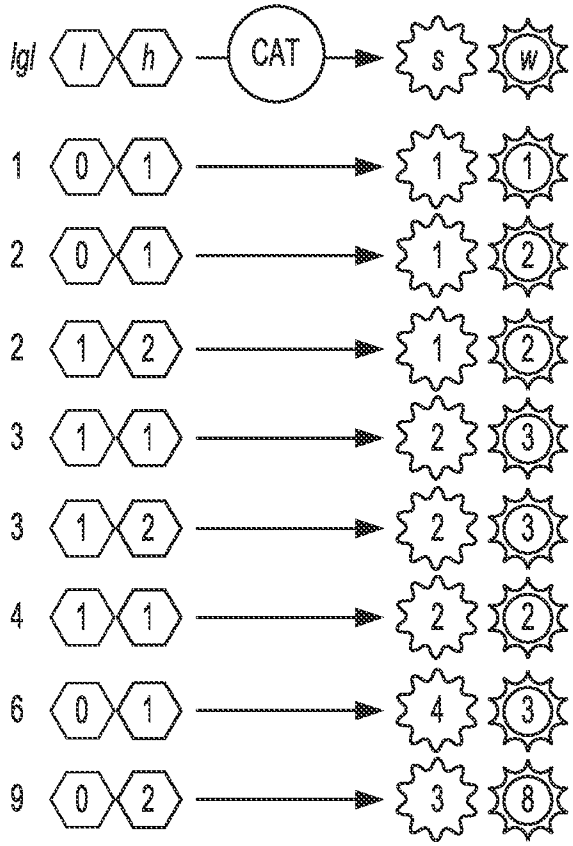
Figure 5:
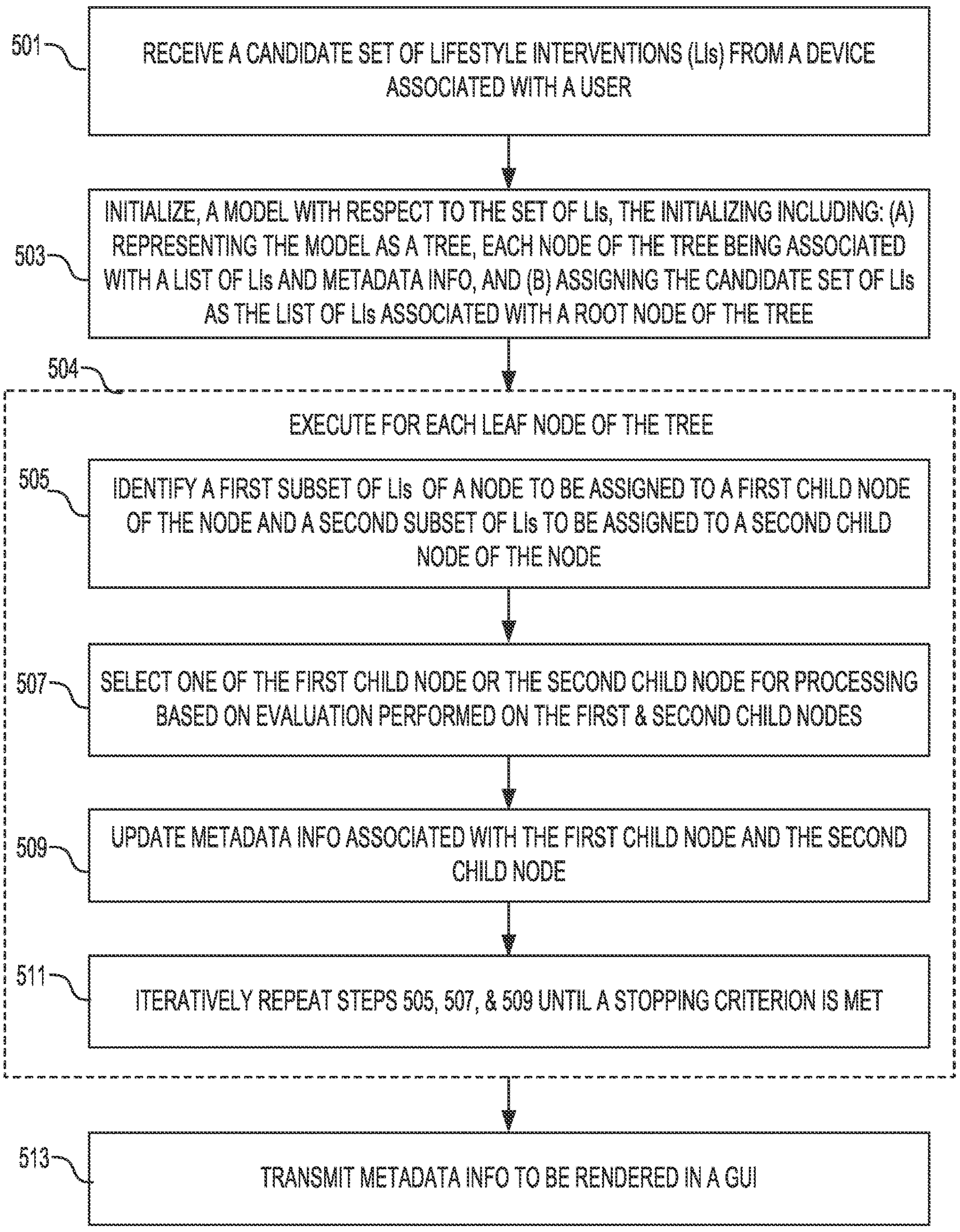
FIG. 5 depicts an exemplary flow diagram illustrating a process performed by the constrained adaptive group testing (CAGT) algorithm, in accordance with various embodiments.

In what follows, there is described with reference to FIGS. 4A-4C and FIG. 5, operation of a constrained adaptive group testing (CAGT) model according to embodiments of the present disclosure. Specifically, FIGS. 4A-4C illustrate example steps performed by a constrained adaptive group testing (CAGT) algorithm/model employed by the ALO server, and FIG. 5 depicts an exemplary flow diagram illustrating a process performed by the constrained adaptive group testing (CAGT) algorithm/model, in accordance with various embodiments.

According to some embodiments, the CAGT model is encoded as a tree e.g., a binary tree that connects a set of nodes denoted by $g_i$. Each $g_i$, represents a set of LIs (referred to herein as a list of LIs) with unknown potency, as well as l and h integers that bound the number of potent LIs in the set. The tree represents nested sets of LIs where the LIs of a non-leaf node are comprised of the LIs of its children, and sibling nodes are disjoint (i.e., have no shared LI). The CAGT model includes three steps in each round of execution, i.e., a first step (referred to herein as a next round function), a second step referred to herein as an obtain potency step, and a third step that is referred to herein as an update CAGT model step.

In step 1, i.e., the next_round function iterates through the leaf nodes and simulates the next round using each node. Doing so, leads to alternative trees. The leaf node g that leads into tree pairs (two trees per g due to two possible potencies) with best potential (i.e., minimum |R|), is chosen for the next round. The optimal number of LIs for next round ($|R_i|$) is identified using a CAGT catalog, given |g| and the corresponding 1 and h from g. It is appreciated that any subset of size $|R_i|$ from g can be selected as $R_i$ for the next round. In one implementation, the subset is chosen in a random manner.

In step 2, the potency of $R_i$ is determined as $r_i$ by the individual. In step 3, the model uses Ri and ri to split the g node and subsequently revise the tree which can lead into updated set of impotent LIs ($V_0$) and set of potent LIs ($V_1$). It is appreciated that revisions are made in the tree based on criteria listed in Table 1 below. Further, it is noted that revising one node, can trigger revisions across the tree using the "trigger revision" column of Table 1, which names the nodes that should be subsequently verified against the criteria enabling an efficient method for finding all the nodes that need verification.

TABLE 1

Criteria used to revise the CAGT tree in each round. Once a node g satisfies a revision criterion, the corresponding "revision[s]" are applied on g, also leading into revising the "trigger revision" nodes. The LIs under node g are represented by g · V, the number of potent LIs in g · V is bounded by g · l and g · h.

| # | criteria | revision[s] | trigger revision |
|---|---|---|---|
| 1 | g · l = \|g · V\| | V1 ← V1 ∪ g · V<br>model · remove(g) | g · parent |
| 2 | g · h = 0 | V0 ← V0 ∪ g · V<br>remove(g) | g · parent |
| 3 | g · h ≠ 0 &<br>g · parent ≠ None &<br>g · parent · h = g · sibling( ) · l | g · l ← 0<br>g · h ← 0 | g |
| 4 | g · l < Σc · l<br>c∈g · children | g · l ← Σc · l<br>c∈g · children | g |

For sake of illustration, the above-described steps of the CAGT model are described illustratively with reference to FIGS. 4A-4C. As shown in FIG. 4A, the CAGT model receives as input, a candidate set of LIs from a device associated with a user. The candidate set of LIs includes n=9 LIs of unknown potency. As the CAGT model is encoded as a binary tree, the model is initialized with respect to the candidate set of LIs received from the user's device. According to some embodiments, the initialization of the CAGT model includes: (i) representing the model as a tree (e.g., binary tree) including a plurality of nodes, where each node of the tree is representative of a list of lifestyle interventions and includes metadata information associated with the node, and (ii) assigning the set of lifestyle interventions received from the device to the list of lifestyle interventions associated with a root node of the tree (e.g., node represented as g1 in block 401).

Further, each node of the tree has associated metadata information corresponding to the list of LIs associated with the node. By some embodiments, the metadata information includes a first set ($V_0$) including lifestyle interventions from the set of lifestyle interventions that have been determined as being impotent, a second set ($V_1$) including lifestyle interventions from the set of lifestyle interventions that have been determined as being potent, a first parameter n corresponding to a number of lifestyle interventions included in the list of lifestyle interventions associated with the node, a second parameter l corresponding to a minimum number of potent lifestyle interventions included in the list of lifestyle interventions associated with the node, and a third parameter h corresponding to a maximum number of potent lifestyle interventions included in the list of lifestyle interventions associated with the node. As node g1 corresponds to the root node of the tree, the CAGT model sets each of the first set ($V_0$) and the second set ($V_1$) associated with the root node of the tree to a null set. Further, as shown in block 401, the parameter l corresponding to a minimum number of potent Us in the candidate set of Us is 0, whereas the parameter h corresponding to the maximum number of potent Us in the list of lifestyle interventions associated with the root node is set to have a value of 2. It is appreciated that the parameter h is estimated by the ALO server by a process described later with reference to FIG. 7C.

The CAGT model then proceeds to determine an optimum size of the list of interventions that are to be considered next for processing. In one implementation, and as shown in block 403, the CAGT model performs a lookup operation in a CAGT catalog (as shown in FIG. 4C) with inputs being:

n=9, l=0, and h=2. It is appreciated that the catalog includes a plurality of records, where each record includes a mapping of a 3-tuple including parameters {n, l, and h}, to a 2-tuple including parameters {s and w}. Referring to FIG. 4C, which depicts an exemplary CAGT catalog, it is observed that the CAGT catalog entry of n=9, l=0, and h=2 is mapped to the two-tuple having values s=3 and w=8. As the value of parameter s is equal to 3, the CAGT model selects three LIs from the list of LIs associated with node g1. Any selection criteria may be implemented to select the three LIs. For instance, in one implementation, the LIs may be selected in a random fashion. As shown in block 403 of FIG. 4A, the selected LIs from the list of LIs associated with the root node g1 are the first three LIs i.e., LIs 1, 2, and 3, respectively, which forms the set $R_1$.

In the next step, the CAGT model obtains a potency response with respect to set $R_1$. For example, as shown in block 405 of FIG. 4A, the potency response obtained with respect to set $R_1$ has a value of 1. It is noted that a potency response having a value of '0' corresponds to none of the LIs in the set being potent i.e., all LIs are impotent, whereas a potency response having a value of '1' corresponds to one or more LIs in the set being potent. Further, in the next step, as shown in block 407 the CAGT model is updated by splitting node g1 into two child nodes (i.e., left child and right child) and updating the metadata information associated with the nodes. For example, as shown in 409, the original node g1 (of block 401) is split into a right child node g2 (having a list of LIs associated with it being LIs 1, 2, and 3), and a left child node g3 (having a list of LIs associated with it being LIs 4, 5, 6, 7, 8, and 9). Further, metadata information is updated as follows: note that the original node g1 was associated with l=0 and h=2. Upon obtaining the potency response of value '1', as shown in block 409 of FIG. 4A, the l parameter associated with g1 is updated to 1 (as there is at least one potent LI), and the parameter h is maintained at a value of 2.

Further, a first subset of the list of lifestyle interventions (e.g., LIs 1, 2, and 3) associated with the root node is assigned to a first child node of the root node i.e., node represented as g2, and a second subset of the list of lifestyle interventions (e.g., LIs 4-9) associated with the root node is assigned to a second child node of the node i.e., node represented as g3. Note that the parameters l and h associated with node g2 are set to have values l=1 and h=2, respectively, and parameters l and h associated with node g3 are set to have values l=1 and h=2, respectively. Thus, the CAGT model upon one round of execution results in the binary tree represented as 409.

Further, the CAGT model selects one of the first child node and the second child node (i.e., nodes g2 and g3 of block 409) to be utilized for a next round of processing based on an evaluation of each of the first child node and the second child node. FIG. 4B depicts the processing performed on each of the first child node and the second child node in order for the CAGT model to perform the selection. As shown in FIG. 4B, block labeled 420 depicts the processing involved with respect to nodes g2 and g3 in identifying the best leaf node to be used in the next round of iteration of the CAGT model. Specifically, block 421 of FIG. 4B (and the steps depicted below the block) correspond to processing performed on node g2 of block 409 in FIG. 4A, whereas block 423 of FIG. 4B (and the steps depicted below the block) correspond to processing performed on node g3 of block 409 in FIG. 4A.

Referring to block 409 of FIG. 4A, note that with respect to node g2, the metadata includes the following values: n=3 (i.e., number of interventions included in the list of interventions associated with the node) l=1 (i.e., minimum number of potent LIs) and h=2 (i.e., maximum number of potent LIs). Referring to the catalog depicted in FIG. 4C, it is observed that CAGT catalog entry of n=3, 1=1, and h=2 is mapped to the two-tuple having values s=1 and w=3. As the value of parameters is equal to 2, the CAGT model selects two LIs from the list of LIs associated with node g2. This is shown in block 421 of FIG. 4B, where the two selected LIs are LI 1 and 2.

The CAGT model simulates two trees (corresponding to two outcomes of potency responses i.e., potency response of 1 and potency response of 0). In the case of having potency response of 0, the set $V_0$ is updated to include LIs 1 and 2 (as being impotent LIs) and the set $V_1$ is updated to include LI 3 as being a potent LI (i.e., evaluation from previous round). Further, in the case of simulating the potency response of 0, it is noted that node g3, having Us 4-9 (i.e., n=6), and values l=0 and h=1 results in a maximum number of rounds for this leaf node being 3 (i.e., via catalog lookup of n=6, l=0, and h=1). In a similar manner, the CAGT model simulates the case of having potency response of 1, which leads to evaluation of nodes g4 and g5, leading to a total maximum number of rounds being 6. As shown in FIG. 4B, the CAGT algorithm selects for each child node's possible simulated cases, the maximum number of rounds possible i.e., in the example of evaluating block 421, the CAGT model selects a maximum of 3 rounds and 6 rounds (corresponding to the two possible potency response cases).

Similar to the description provided above with respect to the evaluation of node g2, the CAGT model simulates node g3 for both possible outcomes of potency responses i.e., potency response of 1 and potency response of 0. This evaluation is depicted in block 423. As shown in FIG. 4B, the maximum number of rounds in evaluation of node g2 is 5 rounds. According to some embodiments, the CAGT model in selecting one of the child nodes for further processing, selects the node having the minimum of the maximum possible rounds i.e., the CAGT model selects node g3 for further processing (having 5 maximum possible rounds as compared to 6 possible rounds incurred by node g2). It is appreciated that the CAGT model iteratively repeats the above process until a stopping criterion is satisfied e.g., the stopping criterion may correspond to a potency of each lifestyle intervention included in the set of lifestyle interventions being determined as one of potent or impotent.

FIG. 5 depicts an exemplary flow diagram illustrating a process performed by the constrained adaptive group testing (CAGT) model, in accordance with various embodiments. The processing depicted in FIG. 5 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 5 and described below is intended to be illustrative and non-limiting. Although FIG. 5 depicts the various processing steps occurring in a particular sequence or order, this is not intended to be limiting. In certain alternative embodiments, the steps may be performed in some different order or some steps may also be performed in parallel. Furthermore, the process depicted in FIG. 5 may be performed by the ALO server 110 of FIG. 1.

The process commences in step 501, where the ALO server receives a candidate set of LIs from a device (e.g., mobile device 101A) associated with a user. It is noted that the candidate set of LIs is associated with improving a health condition of the user. In step 503, the ALO server initializes a model with respect to the candidate set of Us received in step 501. In some implementations, the initializing performed by the ALO server includes: (i) representing the model as a tree including a plurality of nodes. Each node of the tree is representative of a list of lifestyle interventions and includes metadata information associated with the node, and (ii) assigning the set of lifestyle interventions received in step 501 to the list of lifestyle interventions associated with a root node of the tree. It is noted that the metadata information associated with each node of the tree includes information such as: (i) a first set ($V_0$) including lifestyle interventions from the set of lifestyle interventions that have been determined as being impotent, (ii) a second set ($V_1$) including lifestyle interventions from the set of lifestyle interventions that have been determined as being potent, (iii) a first parameter n corresponding to a number of lifestyle interventions included in the list of lifestyle interventions associated with the node, (iv) a second parameter I corresponding to a minimum number of potent lifestyle interventions included in the list of lifestyle interventions associated with the node, and (v) a third parameter h corresponding to a maximum number of potent lifestyle interventions included in the list of lifestyle interventions associated with the node.

The process then moves to step 504, where a set of processes are executed iteratively (i.e., steps labeled 505-511 in FIG. 5) for each leaf node in the tree. In step 505, the ALO server identifies—a first subset of LIs of a node that are to be assigned to a first child node of the node (e.g., left child node) and a second subset of LIs of the node that are to be assigned to a second child node of the node (e.g., right child node). In some implementations, the number of LIs included in the first subset and the second subset are determined based on a catalog that is generated with respect to the set of lifestyle interventions received from the device. For instance, referring to FIG. 4A and the node depicted in 401, it is observed that the node (g1) has nine LIs in the list of LIs associated with the node. Further, the values of parameter I and h associated with node g1 are 0 and 2, respectively. Based on a lookup operation performed with a catalog (e.g., catalog depicted in FIG. 4C) it is noted that for the combination of n=9, l=0, and h=2, the number of LIs included in the first subset are three (i.e., value of s parameter=3). Thus, in one implementation, three LIs may be randomly selected from the list of LIs associated with node g1 to be assigned to a first child node of g1, whereas the remaining 6 LIs may be assigned to the second child node of g1.

The process thereafter proceeds to step 507, where each of the first and second child nodes are evaluated in order to select one of the child nodes for a next round of processing. As depicted in FIGS. 4A and 4B, the evaluation of each of the first child node and the second child node comprises at least: (a) simulating each of the first subset and the second subset for both potency response values of 0 and 1, (b) identifying, based on a catalog generated with respect to the set of lifestyle interventions, a first result of simulating the model for the first potency response value (e.g., potency response of 0) of the first subset, and a second result of simulating the model for the second potency response value (e.g., potency response of 1) of the first subset, and (c) identifying a first maximum number of rounds of model execution required to determine potencies of lifestyle interventions included in the first subset, and (d) identifying, based on the catalog, a third result of simulating the model for the first potency response value (e.g., potency response of 0) of the second subset, and a fourth result of simulating the model for the second potency response value (e.g., potency response of 1) of the second subset, and identifying a second maximum number of rounds of model execution required to determining potencies of lifestyle interventions included in the second subset. According to some embodiments, the ALO server performs a comparison of the first maximum number of rounds of model execution with respect to the second maximum number of rounds of model execution. Further, the server selects the first child node in response to the first maximum number of rounds of model execution being lower than the second maximum number of rounds of model execution or the second child node in response to the second maximum number of rounds of model execution being lower than the first maximum number of rounds of model execution. It is appreciated that in come implementations, the execution of each child node by the CAGT model, includes the user providing a response (0/1) i.e., potency response 405 as shown in FIG. 4A, to the server with respect to a provided LI set.

The process then moves to step 509, where the ALO server updates the metadata information associated with the first and the second child nodes. An example of updating the metadata information of the child nodes is depicted in FIG. 4A at 409 with respect to nodes g2 and g3 (that are child nodes of the parent node g1). Thereafter, the process moves to step 511 where the ALO server iteratively repeats the processing described in steps 505, 507, and 109 until a stopping criterion is satisfied. In one implementation, the stopping criterion corresponds to a potency of each lifestyle intervention included in the set of lifestyle interventions being determined as one of potent or impotent. Upon completion of the iterative processing of step 504, the process moves to step 513, where the ALO server transmits metadata information (e.g., potency result of each LI included in the candidate set of LIs received in step 501) to be rendered in a graphical user-interface that is displayed on the user's device.

Figure 6A:
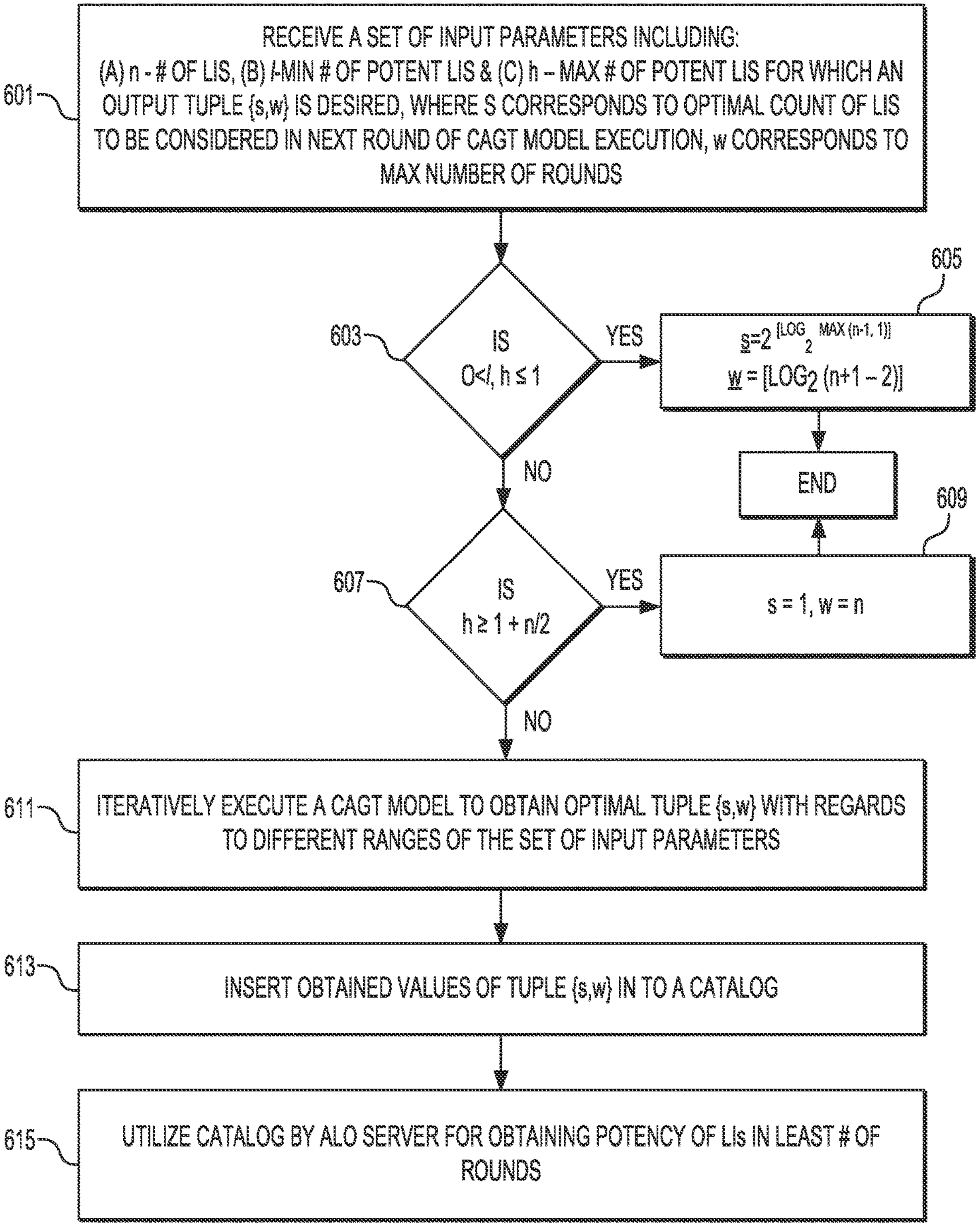
FIG. 6A depicts an exemplary flow diagram illustrating a process to build a catalog, in accordance with various embodiments.

FIG. 6A depicts an exemplary flow diagram illustrating a process to build a catalog, in accordance with various embodiments. The processing depicted in FIG. 6A may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 6A and described below is intended to be illustrative and non-limiting. Although FIG. 6A depicts the various processing steps occurring in a particular sequence or order, this is not intended to be limiting. In certain alternative embodiments, the steps may be performed in some different order or some steps may also be performed in parallel.

The catalog is used by the CAGT model as a lookup table that takes {n, l, h} as input and provides {s,w} as the output, where the parameter n corresponds to a number of lifestyle interventions, l corresponds to a minimum number of potent lifestyle interventions, h corresponds to a maximum number of potent lifestyle interventions, s corresponds to an optimal count of lifestyle interventions to be considered for execution of the model, and w corresponds to a maximum number of executions of the model that is required to obtain potencies of n lifestyle interventions.

According to some embodiments, a dynamic programming strategy is used to build the CAGT catalog based on the fact that in each round of CAGT, either the number of Us in individual leaf nodes decreases, or their corresponding bounds (l and h) tighten. Therefore, to find the optimal (sy, wy) of new catalog record y: (ny, ly, hy), if the catalog is built to contain (sx, wx) for all the records x:(nx, lx, hx) where nx≤ny and (lx, hx) are tighter than (ly, hy). Thus, one can execute simulations of the CAGT algorithm using all valid sy values for the initial next_round of a CAGT run in order to find the sy that minimizes wy. Note that during each simulation, the sy value is only used for the initial "next_round" call when only the root node exists. All the other catalog lookups rely on optimal (sx, wx) values calculated beforehand. For the base cases of this dynamic programming algorithm, we rely on known optimal (s, w) values. Furthermore, the CAGT catalog building algorithm of FIG. 6A operates on the following principle: when 0≤l & h≤1, the binary splitting algorithm is optimal with a value of $s=2^{\lfloor \log_2 max\ (n-1,1) \rfloor}$ leading into w=⌈log 2(n+1−l)⌉, while for h≥1+n/2, using s=1 is optimal which leads to w=n.

The process as depicted in FIG. 6A commences in step 601, where a set of parameters {n, l, h} are received as input for which the tuple {s,w} is desired. In step 603 a first query is executed to determine whether the parameters l and h are in the range of [0-1]. If the response to the query is affirmative, the process moves to step 605, else if the response to the query is negative, then the process moves to step 607. In step 605, the value of parameter s returned by the process is $s=2^{\lfloor \log_2 max\ (n-1,1) \rfloor}$ and the value of the parameter w returned is:w=⌈log 2(n+1−l)⌉. Upon returning the values of parameters s and w in step 605, the process terminates.

In step 607, the process executes another query to determine whether the condition of h≥1+n/2 is satisfied. If the response to the query is affirmative, then the process moves to step 609, else, if the response to the query is negative, then the process moves to step 611. In step 609, the value of parameters returned by the process is s=1 and the value of the parameter w returned is: w=n.

In step 611, the CAGT model (described with reference to FIG. 5) is iteratively executed to obtain tuple {s, w} with regard to different ranges of the set of input parameters. Details pertaining to this step are described next with reference to FIG. 6B. In step 613, the values of the tuple {s, w} obtained via the execution performed in step 611 are inserted into the catalog. In step 615, the built catalog is utilized by the ALO server (FIG. 3) in obtaining potencies for an input set of LIs in a minimum number of rounds of model execution.

Figure 6B:
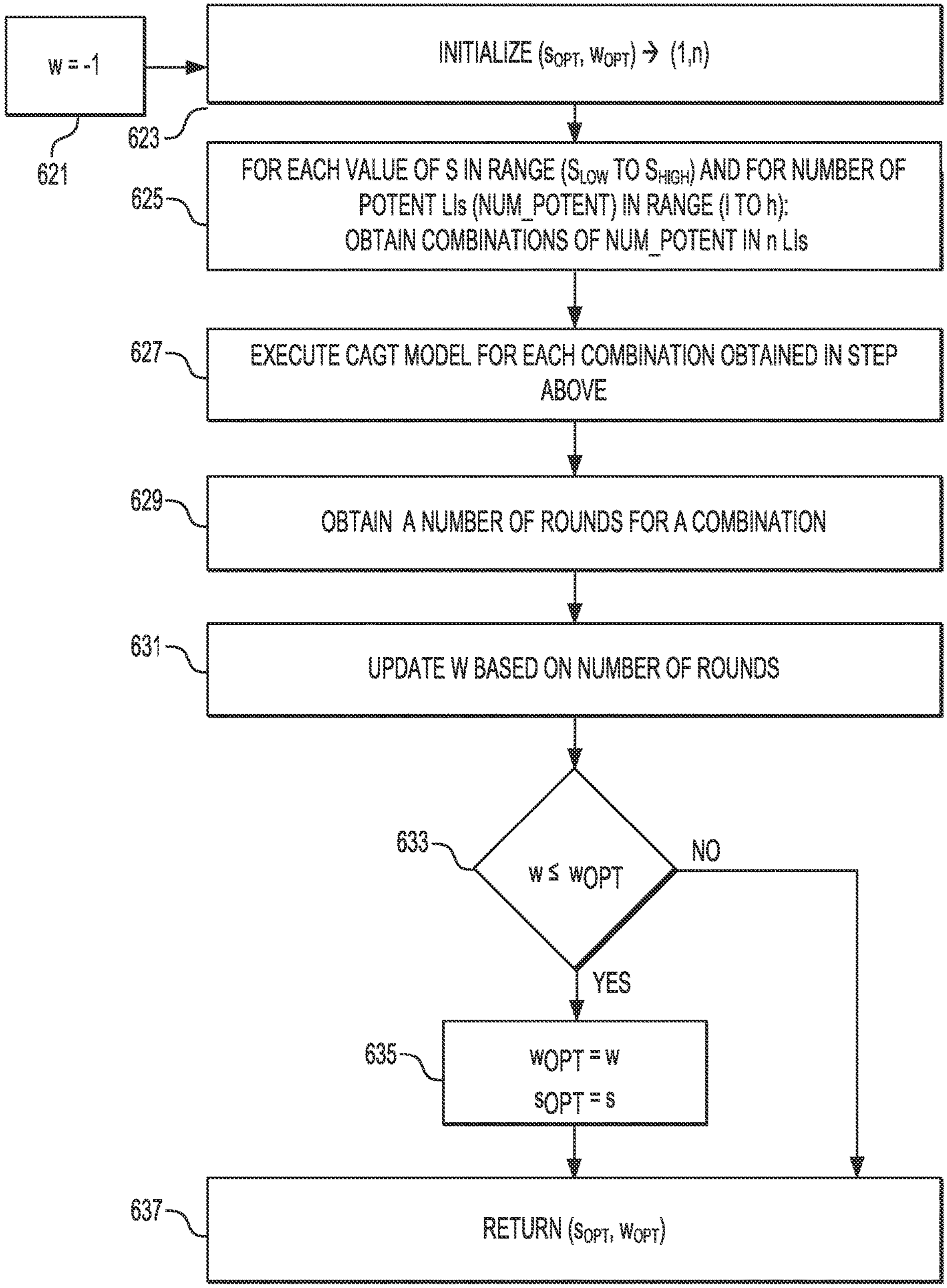
FIG. 6B depicts an exemplary detailed flow diagram illustrating an iterative process performed by the CAGT algorithm in building the catalog, in accordance with various embodiments.

Turning now to FIG. 6B there is depicted an exemplary detailed flow diagram illustrating an iterative process performed by the CAGT algorithm in building the catalog, in accordance with various embodiments. The processing depicted in FIG. 6B may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 6B and described below is intended to be illustrative and non-limiting. Although FIG. 6B depicts the various processing steps occurring in a particular sequence or order, this is not intended to be limiting. In certain alternative embodiments, the steps may be performed in some different order or some steps may also be performed in parallel.

The process commences in step 621 where a value of parameter w is initialized to −1. In step 623, a pair of temporary parameters {$s_{opt}$, $w_{opt}$} are set to {1, n} respectively. Note that the value of parameter s=1 and w=n corresponds to the worst-case scenario that requires n rounds to determine potencies of LIs in a given set of n LIs.

In step 625, for each value of parameters in the range from $s_{low}$=2 to $s_{high}=2^{\lfloor \log_2 max\ (n-1,1) \rfloor}$ and for value of a parameter (NUM_POTENT) in the range 1 to h, all combinations of having (NUM_POTENT) LIs in a set of n LIs is executed. It is appreciated that each combination corresponds to a binary vector that has a length of n and (NUM_POTENT) number of '1's' in the vector (i.e., n−(NUM_POTENT) '0's' in the vector). The process thereafter proceeds to step 627, where the CAGT model (FIG. 5) is executed for each combination of the vector obtained in step 625. The process in step 629 obtains, for each combination, a number of rounds (represented as parameter 'num_rounds') required via execution of the CAGT model in step 627.

In step 631, the process updates the value of parameter w by: w=max (w, 'num_rounds'). In step 633 a query is executed to determine whether the value of w is less than equal to the value of parameter $w_{opt}$. If the response to the query is affirmative, the process moves to step 635 where the value of parameter $w_{opt}$ is set to be w, and the value of parameter $s_{opt}$ is set to be s. If the response to the query is negative, the process proceeds to evaluate the next combination. Upon all combinations being processed, in step 637, the process returns the value of the tuple {$s_{opt}$, $w_{opt}$}.

Figure 7A:
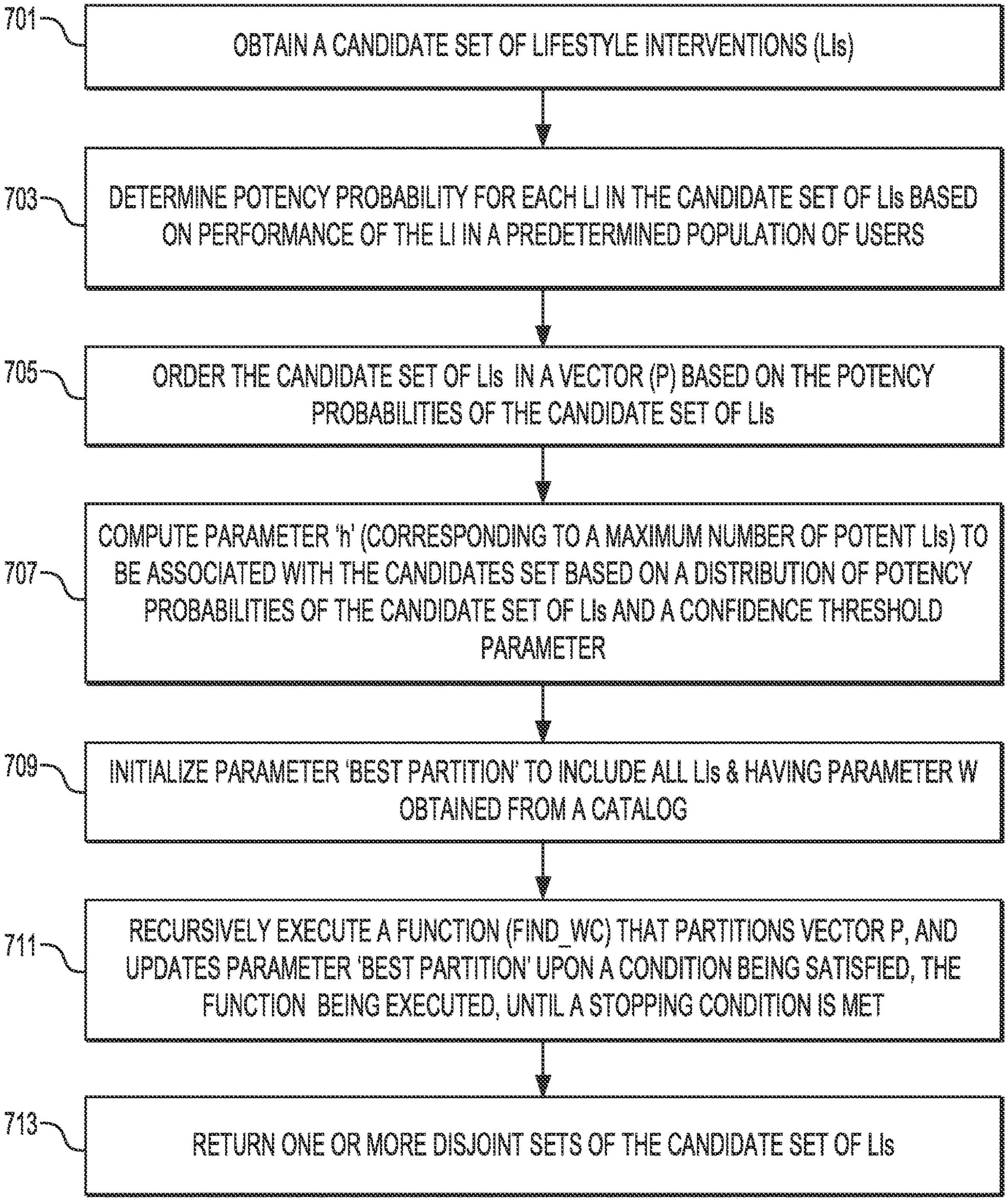
FIG. 7A depicts an exemplary flow diagram illustrating a process of partitioning an input set of candidate lifestyle interventions (LIs), in accordance with various embodiments.

FIG. 7A depicts an exemplary flow diagram illustrating a process of partitioning an input set of candidate lifestyle interventions (LIs), in accordance with various embodiments. The processing depicted in FIG. 7A may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 7A and described below is intended to be illustrative and non-limiting. Although FIG. 7A depicts the various processing steps occurring in a particular sequence or order, this is not intended to be limiting. In certain alternative embodiments, the steps may be performed in some different order or some steps may also be performed in parallel.

According to some embodiments, potency probability of LIs, and the CAGT catalog are used to create an optimal LI partition (i.e., disjoint sets of LIs) to minimize the expected number of CAGT rounds needed while the maximum number of CAGT rounds is also bounded. In one implementation, this is performed in two steps—in the first step, the optimal LI partition is created to minimize the maximum number of CAGT rounds needed given the LI potency probabilities and the CAGT catalog. In the second step, a new optimal LI partition is created in order to minimize the expected number of CAGT rounds while the maximum number of rounds used remains bounded bellow a user defined threshold. In some implementations of the CAGT algorithm, the second step may be optional and the input set of candidate LIs are partitioned based on the first step to minimize the expected number of CAGT rounds (i.e., iterations required to determine the potency of each LI). It is appreciated that when the prevalence of potent Us is high, individual testing is more efficient than group testing. More generally, to achieve optimal performance, Us can be partitioned into disjoint sets based on their potency probabilities such that group testing is performed independently in each set (and with different group testing parametrizations)

Figure 7B:
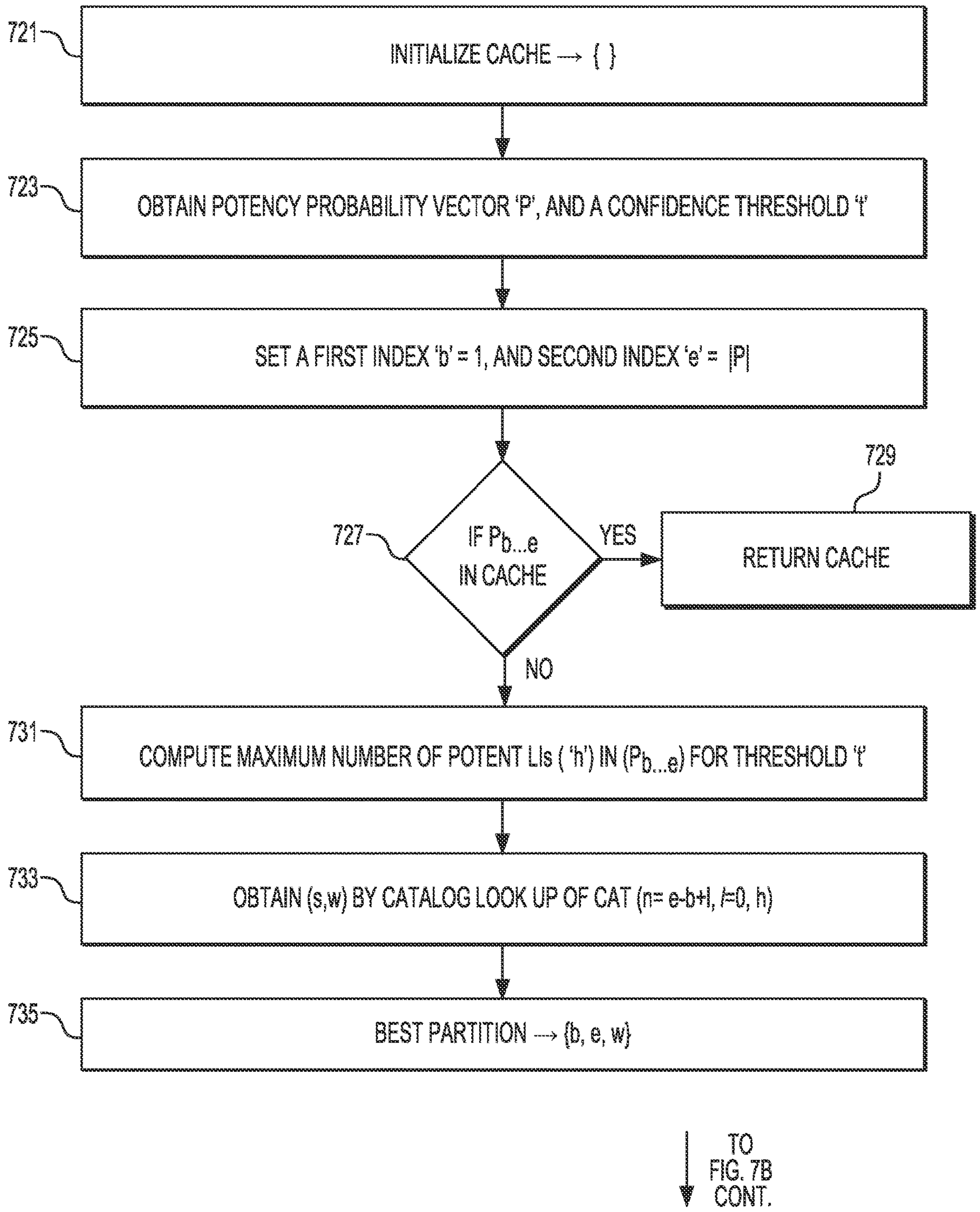
FIG. 7B depicts an exemplary flow diagram illustrating a recursive process in partitioning the input set of candidate lifestyle interventions (LIs), in accordance with various embodiments.
Figure 7B:
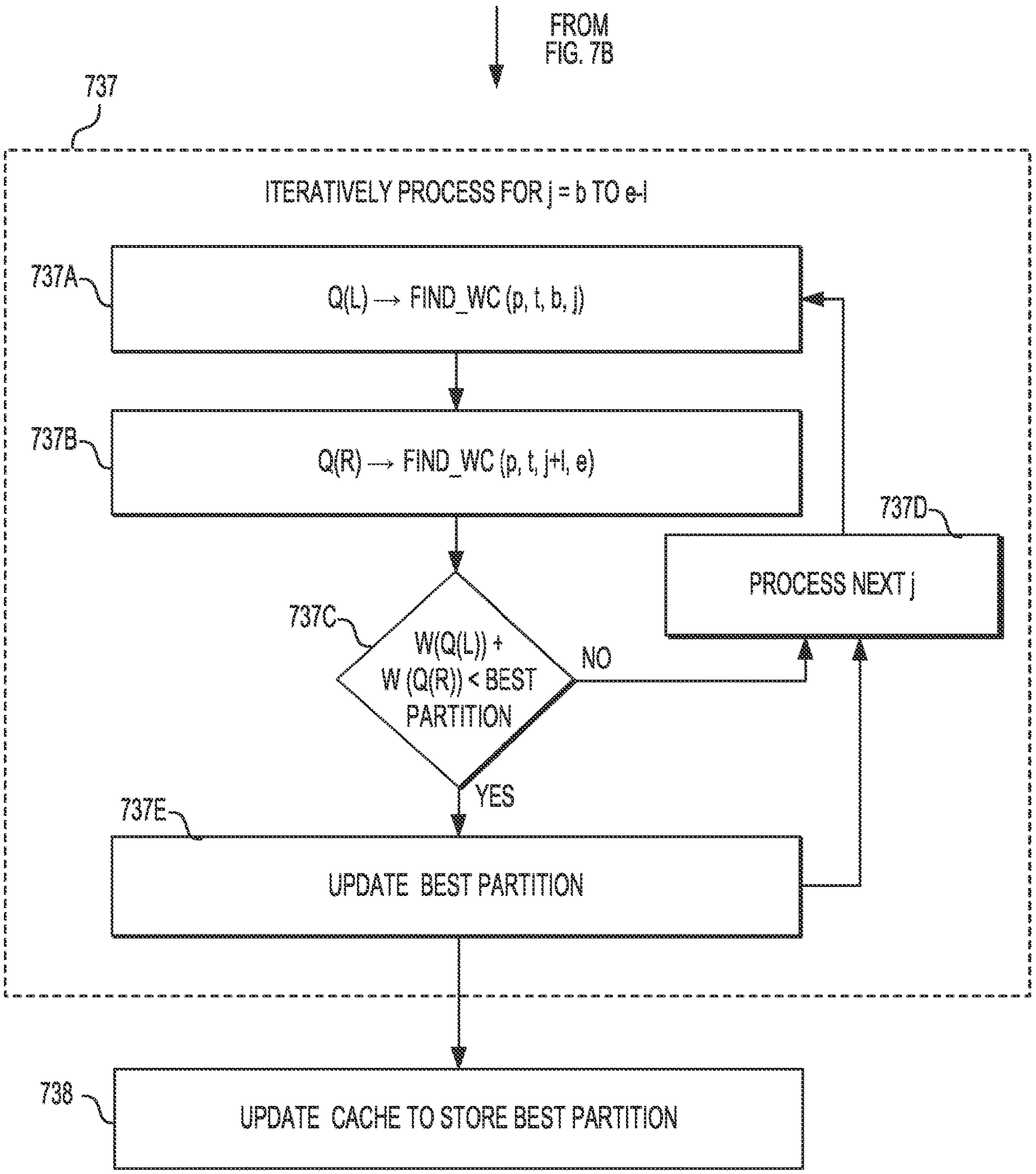
Figure 7C:
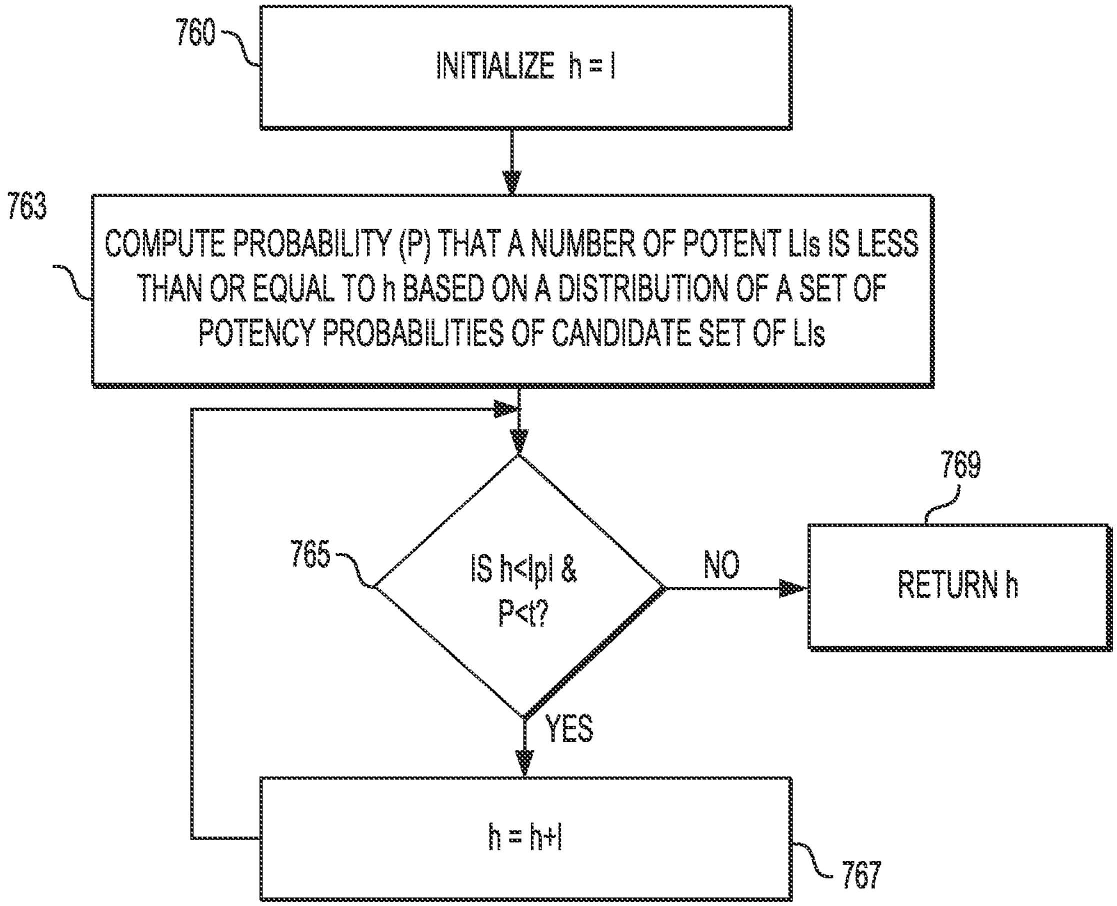
FIG. 7C depicts an exemplary flow diagram illustrating a process of estimating a maximum number of potent lifestyle interventions included in a set of lifestyle interventions, in accordance with various embodiments.

The flowcharts depicted in FIGS. 7A-7C can be executed in order to find the optimal maximum number of CAGT rounds that are needed for discovering the potent LIs (referred to herein by set w) by a function (referred to herein as a FIND_WC function). At a high-level, the processing performed in order to identify the optimal partitions of the candidate set of LIs can be described by the following steps: First, the LIs are reordered based on LI potency probability vector p such that $0 \le p_1 \le p_2 \le \ldots \le p_N \le 1$. Second, the process calculates/estimates parameter h as the maximum number of potent LIs using the Poisson binomial distribution of p and a confidence threshold of $t \in [0,1]$(e.g., 0.95). Third, we consider a best_partition to be all the LIs relating to p with a w* that is returned from the CAGT catalog for (|p|,0, h). Fourth, we execute function find_wc* for $p_{1 \ldots j}$ and $p_{j \ldots |p|}$ recursively $\forall j \in [1, |p|]$ and update best_partition if the returned partition pairs by the two FIND_WC calls are better than the current best_partition.

It is noted that in order to avoid duplicate runs of function (FIND_WC), we check the input p against a lookup table (named cache) in the beginning and only calculate the answer on the first occurrence. Further, in function FIND_WC, 'b' and 'e' are indices of the beginning and end LIs respectively with default values of b='1' and e='|p|'. It is noted that the partition algorithm depicted in FIGS. 7A-7C outputs disjoint sets of LIs (amounting to partition called Q+) such that subjecting individual sets Q to the CAGT algorithm leads into optimal maximum number of CAGT rounds that are needed for discovering the potent LIs. Further, the notation Q(l) is used to represent a left partition of set Q and Q(r) is used to represent a right partition of set Q.

Referring to FIG. 7A, the process commences in step 701, where a candidate set of LIs is received by the ALO server. In step 703, potency probability of each LI in the candidate set of LIs is determined based on a performance of the LI with respect to a predetermined population of users. In step 705, the candidate set of LIs is ordered based on the determined potency probabilities in step 703 e.g., ordered in increasing order of probabilities (e.g., $p_1 \le p_2 \le \ldots \le p_N$). In step 707, a parameter h (corresponding to a maximum number of potent LIs in the candidate set of LIs) is estimated based on a distribution of potency probabilities of the candidate set of LIs and a predetermined confidence threshold. Details regarding the estimation of parameter h are provided below with reference to FIG. 7C. In step 709, a parameter best_partition is initialized to include all LIs, wherein the maximum number of rounds (w) is obtained from the CAGT catalog.

The process then moves to step 711, where a function (FIND_WC) is recursively executed that partitions vector p and updates parameter best_partition upon a condition being satisfied. It is appreciated that the function is executed recursively until a stopping condition is satisfied. Details pertaining to step 711 are described next with reference to FIG. 7B. Upon completion of the recursive execution of step 711, the process in step 713 returns one or more disjoint sets of the candidate set of LIs.

Turning now to FIG. 7B, there is depicted an exemplary flow diagram illustrating a recursive process in partitioning the input set of candidate lifestyle interventions (LIs), in accordance with various embodiments. The processing depicted in FIG. 7B may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 7B and described below is intended to be illustrative and non-limiting. Although FIG. 7B depicts the various processing steps occurring in a particular sequence or order, this is not intended to be limiting. In certain alternative embodiments, the steps may be performed in some different order or some steps may also be performed in parallel.

The process commences in step 721, where a cache is initialized to a null set. Note that the cache is utilized to avoid duplicate runs of function (FIND_WC). In step 723, a potency probability vector (p) and a confidence threshold (t) are obtained. In step 725, a first index b is set to 1 and a second index e is set to |p|. In step 727, a query is executed to determine whether vector $p_{b \ldots e}$ is included in the cache. If the response to the query is affirmative, then the process moves to step 729, wherein the process returns the cache. If the response to the query is negative, then the process moves to step 731. In step 731, the process estimates the parameter h (i.e., maximum number of potent LIs in vector $p_{b \ldots e}$, corresponding to confidence threshold parameter t. Details pertaining to the estimation of parameter h are described next with reference to FIG. 7C. In step 733, values of parameters {s, w} are obtained via a catalog lookup of the {n=e−b+l, l=0, h}. In step 735, the process assigns the parameter best_partition as corresponding to values of first index (b) and second index (e), wherein the maximum number of CAGT rounds is parameter w obtained from step 733. It is noted here that if the value of parameter b=e, the best_partition is returned to the user.

The process then moves to step 737, where steps 737A to 737E are iteratively executed for different values of parameter j ranging from j=b to j=e−1. Specifically, in step 737A, the process executes function FIND_WC for a left partition of set Q (represented as Q(L)) corresponding to parameters p, t, b, and. Further, in step 737B, the process executes function FIND_WC for a right partition of set Q (represented as Q(R)) corresponding to parameters p, t, j+1, and e. It is noted that a number of rounds corresponding to the left and right partitions (denoted as W(Q(L) and W(Q(R)), respectively) can be obtained via a catalog lookup operation.

The process then moves to step 737C, wherein a query is executed to determine whether the sum of number of rounds of the left and right partitions i.e., W(Q(L)+W(Q(R)) is less than the number of rounds corresponding to the best partition stored in the cache. If the response to the query is negative, the process moves to step 737D where the value of parameter j is incremented and steps 737A and 737B are repeated. However, if the response to the query in step 737C is affirmative, the process moves to step 737E, where the best partition is updated to reflect the partition that corresponds to the left and right partitions of steps 737A and 737B, whereafter the process loops back to process the next value of parameter j. It is noted that upon completion of the iterative process of step 737, in step 738, the cache is updated to store the best partition.

FIG. 7C depicts an exemplary flow diagram illustrating a process of estimating a maximum number of potent lifestyle interventions included in a set of lifestyle interventions, in accordance with various embodiments. The processing depicted in FIG. 7C may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 7C and described below is intended to be illustrative and non-limiting. Although FIG. 7C depicts the various processing steps occurring in a particular sequence or order, this is not intended to be limiting. In certain alternative embodiments, the steps may be performed in some different order or some steps may also be performed in parallel.

The process commences in step 760, where value of parameter h is initialized to 1. Thereafter, in step 763, the process computes a probability P (represented as $Pr_p(K \leq h)$) corresponding to a probability that a number of potent Us is less than equal to h based on a distribution of a set of potency probabilities (e.g., Poisson binomial distribution) of the candidate set of Us. In step 765, a query is executed to determine whether h is less than $|p_1$ and probability P (computed in step 763) is less than parameter t i.e., the confidence threshold. If the response to the query is negative, the process moves to step 769 to return the value of parameter h. However, if the response to the query is affirmative, the process moves to step 767, where the value of parameter h is incremented by 1 and the process thereafter loops back to step 765.

The processes described with reference to FIGS. 7A to 7C describe a manner of partitioning an input set of candidate Us, such that the maximum number of rounds (i.e., iterations) required by the CAGT model are minimized. According to some embodiments, the input set of candidate Us may be partitioned in disjoint sets such that the average number of rounds required by the CAGT algorithm are minimized. In this embodiment, a new parameter named 'ex' (that is predetermined by the user) is introduced and corresponds to the number of extra rounds permitted in addition to w rounds (as described with reference to FIGS. 7A and 7B), thereby making the total number of rounds (wex) equal to w+ex.

In this embodiment, we allow an extra round in which the LIs of a disjoint set will be followed simultaneously by the individual, as long as the total of the maximum number of CAGT rounds from all disjoint sets is not greater than wex. In doing so, we minimize the expected number of CAGT rounds by identifying the optimal partition (i.e., disjoint sets of LIs) along with the sets that will have an extra initial CAGT round. The expected number of rounds for a set with extra initial round can be calculated using the weighted average $p_0+(1-p0)\times w1$ where p0 is $Pr_p(K \leq 0)$ (probability that the initial extra round returns a '0'), and w1 is the maximum number of CAGT rounds for the set if the initial extra round returns a '1'. This optimal partition (calculated by find_Q*) is identified by finding the sets in which the extra initial round provides the maximum benefit towards the objective. The algorithm relies on the fact that if there is only one extra initial round available (ex=1), it should be used for a set who's LIs have lower potency probabilities.

Figure 8:
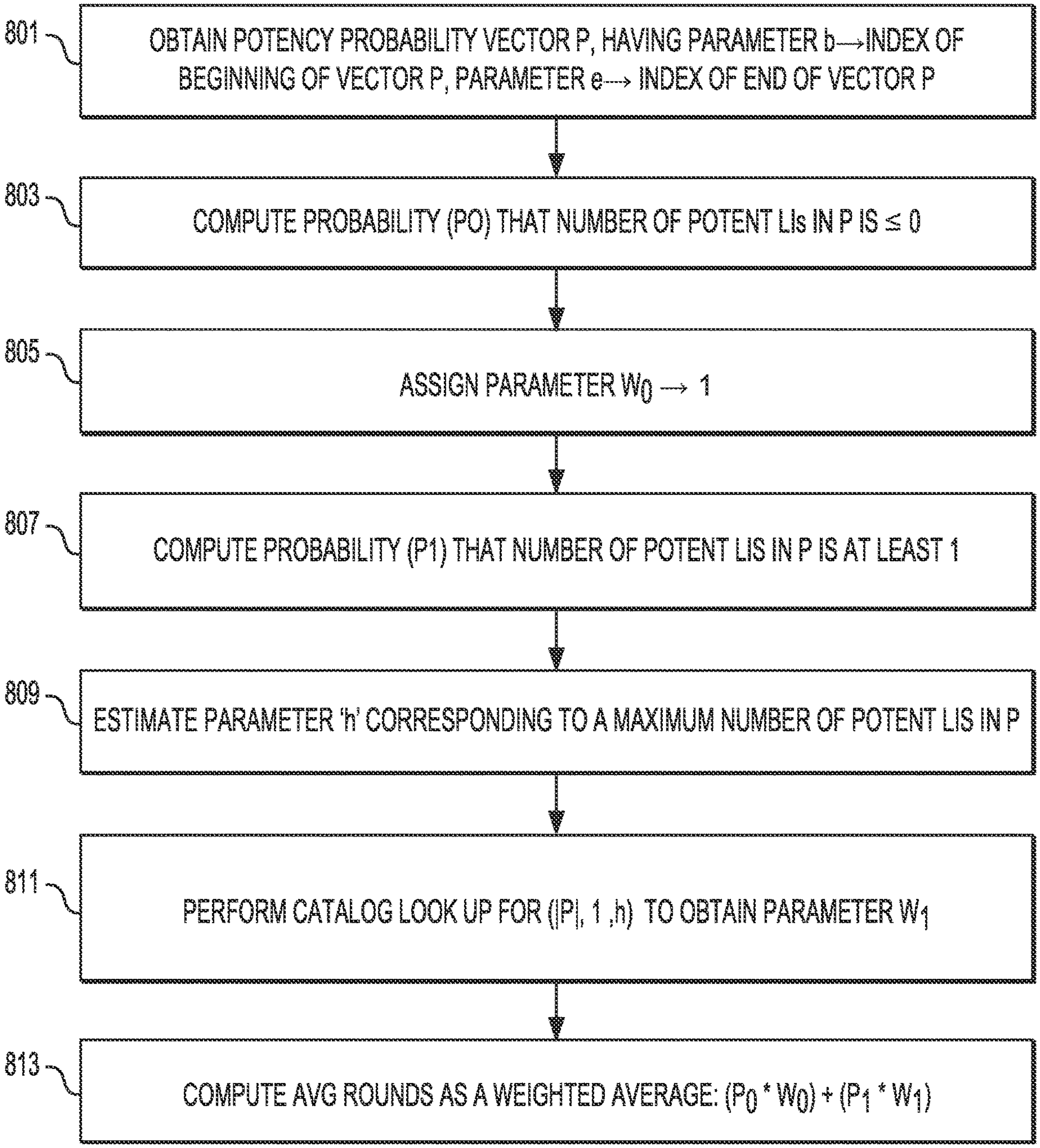
FIG. 8 depicts an exemplary flow diagram illustrating a process of computing average number of CAGT rounds if an extra initial round is used, in accordance with various embodiments.

FIG. 8 depicts an exemplary flow diagram illustrating a process of computing average number of CAGT rounds if an extra initial round is used, in accordance with various embodiments. The processing depicted in FIG. 8 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 8 and described below is intended to be illustrative and non-limiting. Although FIG. 8 depicts the various processing steps occurring in a particular sequence or order, this is not intended to be limiting. In certain alternative embodiments, the steps may be performed in some different order or some steps may also be performed in parallel.

The process commences in step 801, where a potency probability vector (p) is obtained. The vector is associated with a first parameter 'b' that corresponds to an index of the beginning of the vector and a second parameter 'e' that corresponds to an index associated with the end of the vector. In step 803, the process computes a probability (P0) which is represented as $Pr_p(K \leq 0)$ and corresponds to probability that a number of potent LIs in p is less than equal to zero. The process then proceeds to step 805 where parameter W0 is assigned a value of 1. In step 807, the process computes probability (P1) which corresponds to probability that a number of potent LIs in p is at least 1. It is appreciated that probability P1 may be computed as 1−P0. Thereafter, the process moves to step 809, where parameter h that corresponds to a maximum number of potent LIs in vector p is estimated. Note that parameter h may be estimated based on the method described previously with reference to FIG. 7C. In step 811, the process determines the value of parameter w1 by performing a catalog lookup operation for the combination {n=|p|, l=1, h}. The value of w1 is determined as the number of rounds obtained from the catalog lookup operation of {n=|p|, l=1, h}+1. In step 813, the process computes the average number of rounds required as a weighted average: (P0*W0)+(P1* W1). In what follows, there is provided a detailed description of the performance evaluation of the above-described ALO server and the CAGT algorithm.

Evaluation Framework

Figure 9:
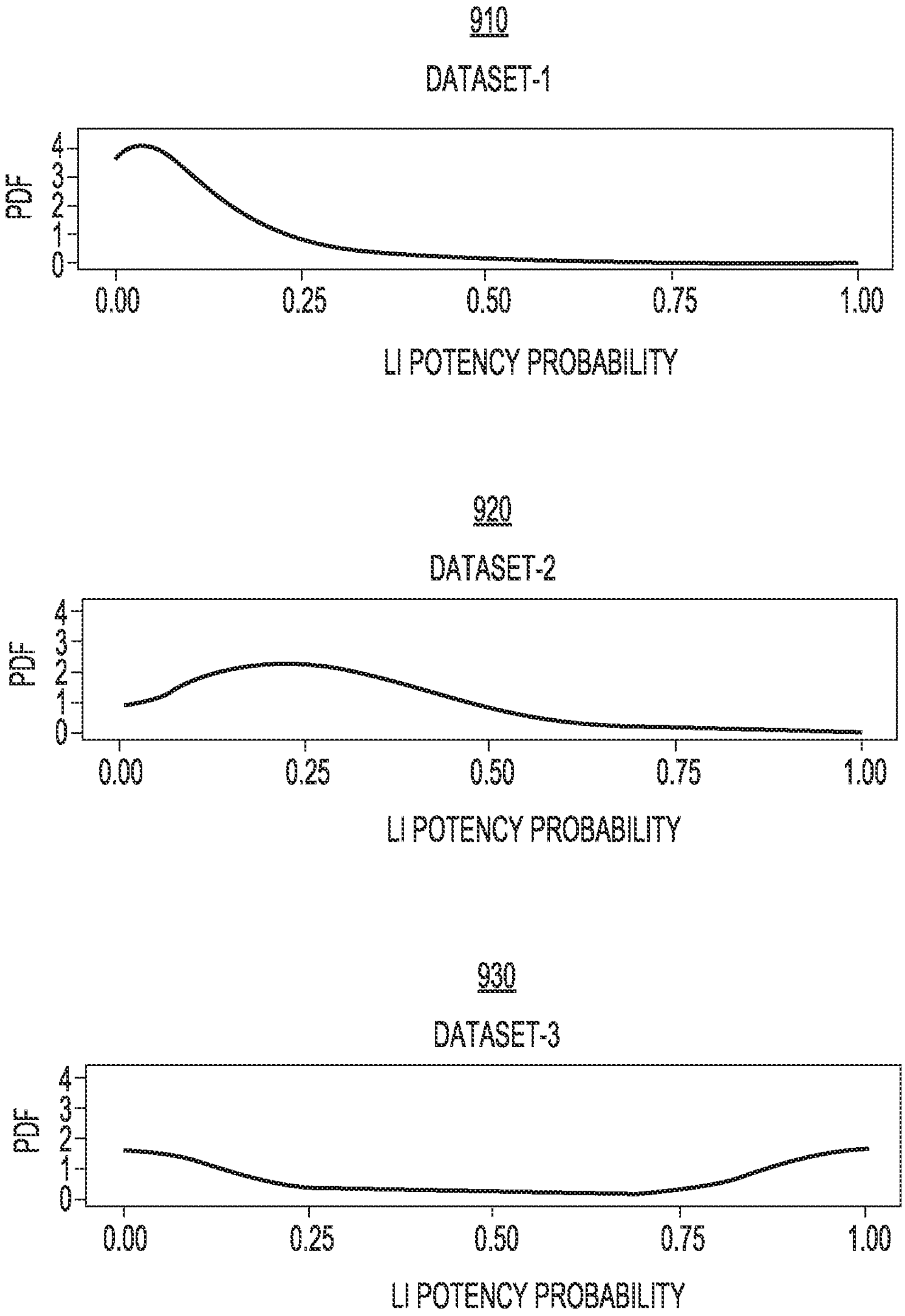
FIG. 9 depicts exemplary datasets used in performance evaluations, in accordance with various embodiments.

In some embodiments, synthetic as well as real data was utilized for evaluating performance of the ALO server and its components. For instance, synthetic data was used for robustness and sensitivity analysis, whereas real data was used for food intolerance and allergy identification applications. For synthetic data, the data is generated from three sets of LI potency probabilities, each with 50 values that follow beta distributions with three different shapes (Dataset-1: $\alpha$=0.5, $\beta$=5.0, Dataset-2: $\alpha$=2.0, $\beta$=6.0, and Dataset-3: $\alpha$=0.1, $\beta$=0.1). FIG. 9 depicts exemplary datasets used in evaluating performance of the ALO server.

Further, 200 values are generated for each LI potency probability of the prior step following Bernoulli distributions parametrized by each probability value. This provides us with three datasets that each include a 200×50 matrix that represents the LI potencies for 200 individuals, along with the set of LI potency probabilities that were used to generate each. Finally, for each set of LI potency probabilities in a dataset, we generate nine sets of noisy LI potency probabilities by adding different levels of white noise with standard deviation (SD) values that ranged from 0.05 to 0.5. The noisy LI potency probabilities are clamped in the 0-1 range (i.e., set to 0 if less than 0, and set to 1 if greater than 1).

In the case of real data, according to some embodiments, there are defined two sets of LIs, one for management of food intolerances in IBS and another for management of allergic food reactions. In both LI sets, an LI corresponds to the elimination of a particular food from the patient's diet, and the LI's potency probability corresponds to the fraction of individuals in which a given food triggers adverse symptoms. First, we extract the LIs and their potency probabilities from published studies of IBS and food allergies separately. Secondly, we use the Poisson distribution parametrized by the average number of potent LIs from each study (e.g., reported as 7 in the IBS study and estimated as 1.43 for the food allergy study given their reported statistics), in order to generate one-thousand integers for each study, where each integer corresponds to the number potent LIs in a given individual. Finally, we randomly assign individual potency values (0|1) for the LIs in each patient given the number of potent LIs in each, and the potency probability of each LI that was extracted from the corresponding study. This provides us with an IBS dataset with 56 LIs, and a food allergy dataset with 19 LIs, each with the corresponding potency probabilities, and one thousand LI potency profiles that adhere to the reported summary statistics.

According to some embodiments, for evaluation metrics we use the average and median number of rounds needed for identifying the LI potencies of individuals. We compare the performance of the ALO method to a known spatial inference vertex cover (SPIV) method. For each dataset, first the optimal hyper-parameters are identified using grid search on half of the dataset, then the evaluations are performed on the remaining records. In each case, a maximum of fifty pair of hyper-parameter values were examined for ex and t in the ALO method, while for the SPIV method, a maximum of hundred hyper-parameter value pairs were examined for its epsilon, and t parameters including the default parameter values.

Figure 10:
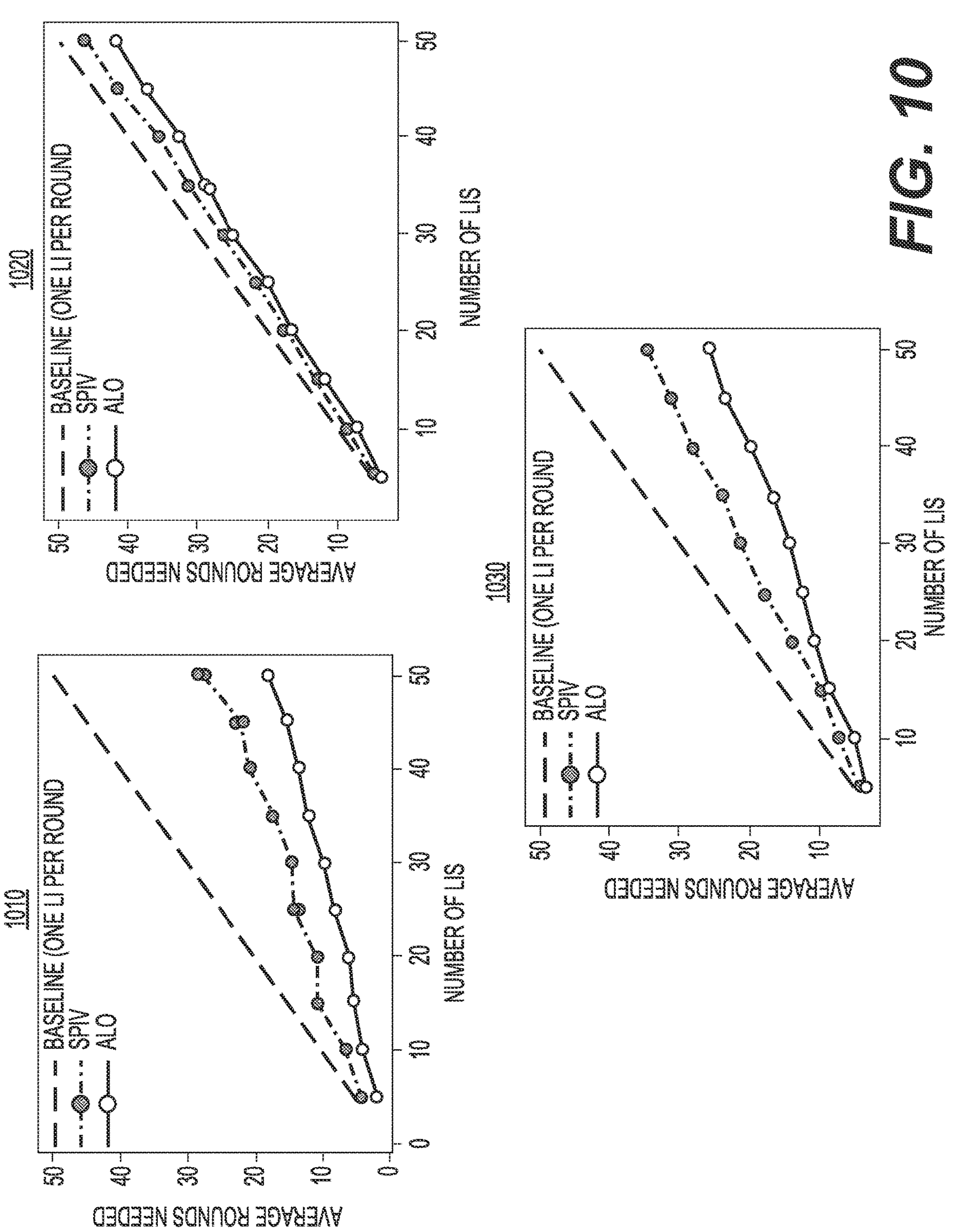
FIG. 10 depicts exemplary graphs illustrating average number of rounds required to identify potent Us in a set of Us, in accordance with various embodiments.
Figure 11:
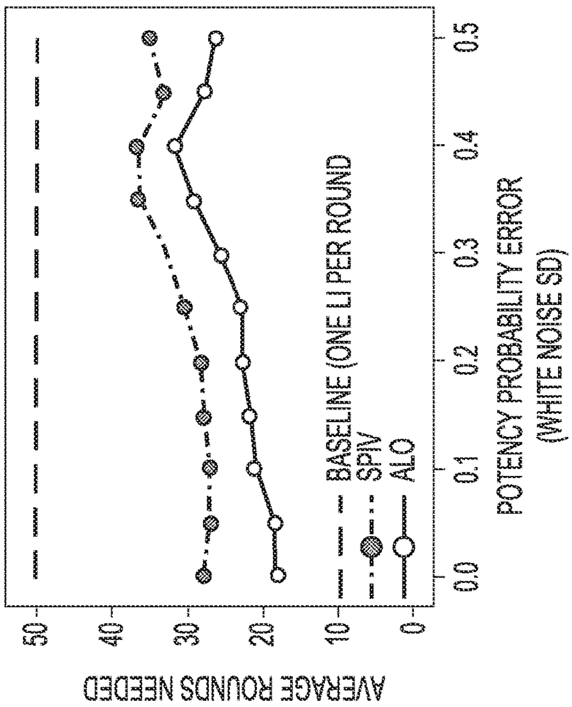
FIG. 11 depicts exemplary graphs illustrating robustness to standard deviation of white noise added to potency probabilities, in accordance with various embodiments.
Figure 11:
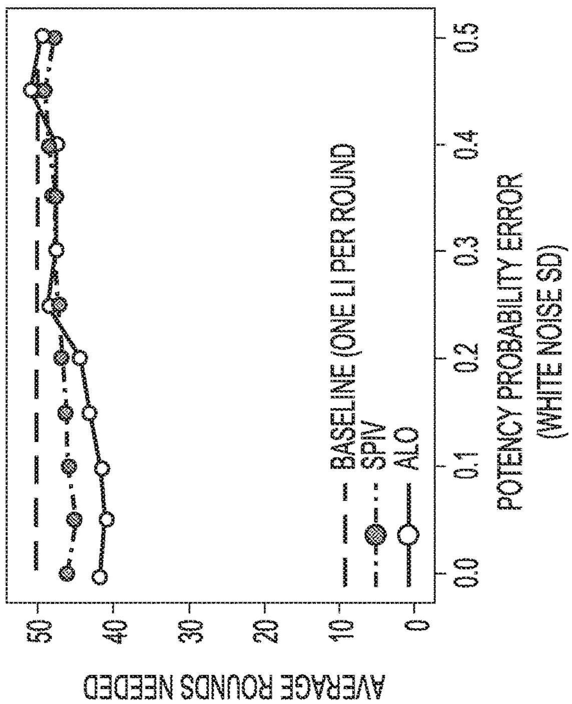
Figure 11:
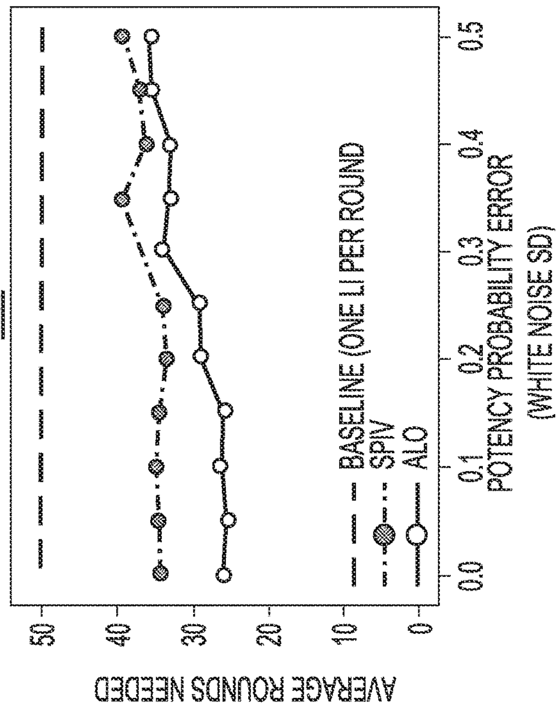

In some embodiments, we generated three datasets with various levels of homogeneity (e.g., Dataset-1 (910), Dataset-2 (920), and Dataset-3 (930) as shown in FIG. 9), for evaluating the sensitivity of each method to the number of LIs and to the noise in LI potency probabilities. FIG. 10 depicts three graphs 1010, 1020, and 1030 (each corresponding to the datasets 910, 920, and 930 of FIG. 9), which illustrate the average number of rounds needed by each method to identify the potent LIs in hundred individuals for LI subsets having 5 to 50 LIs each. Further, FIG. 11 depicts three graphs 1110, 1120, and 1130 (related to the datasets 910, 920, and 930 of FIG. 9), which illustrate the corresponding method's robustness to the standard deviation (SD) of the added white noise that was added to LI potency probabilities. It is noted that the error bars represent the standard error.

In all cases of performance evaluations, the average rounds needed for identifying the LI potencies increased linearly while the ALO method has the lowest increase, followed by SPIV, and the baseline (as shown in FIG. 10). It is noted that the largest reduction in average rounds needed for ALO compared to the baseline was observed for Dataset-1 (910 in FIG. 9) and Dataset-3 (930 in FIG. 9), in which a large portion of LIs have low potency probabilities (graphs 1010 and 1020 of FIG. 10). Note that this reduction is much lower for Dataset-2 (920 in FIG. 9) in which a lower proportion of LIs have low potency probabilities (graph 1020 of FIG. 10). The addition of white noise to LI potency probabilities increased the average rounds needed by each method (see graphs 1110, 1120, and 1130 of FIG. 11) where methods were evaluated on all 50 LIs while white noise with varying standard deviations (SD) were added to the LI potency probabilities. For example, white noise with SD of 0.5 increased the average rounds needed in Dataset-1 by ALO from 18.2 to 26.5 (45.6%), and by SPIV from 26.9 to 34.7 (29.0%) (see graph 1110 of FIG. 11).

By some embodiments, a gold standard method used in the clinics for identifying foods that cause intolerance or allergic reactions, is the standard elimination diet (SED), during which food challenges are performed. A food challenge is a lifestyle intervention (LI) during which target health symptoms are monitored while a given food item is introduced to the individual's diet for 3 days, then subsequently removed from the diet for another 3 days (note that the number of days may vary). By some embodiments of the present disclosure, there is provided a comparison of ALO with SED as well as another group testing method i.e., the spatial inference vertex cover (SPIV) method for identification of food intolerances and food allergies as described next.

Figure 12:
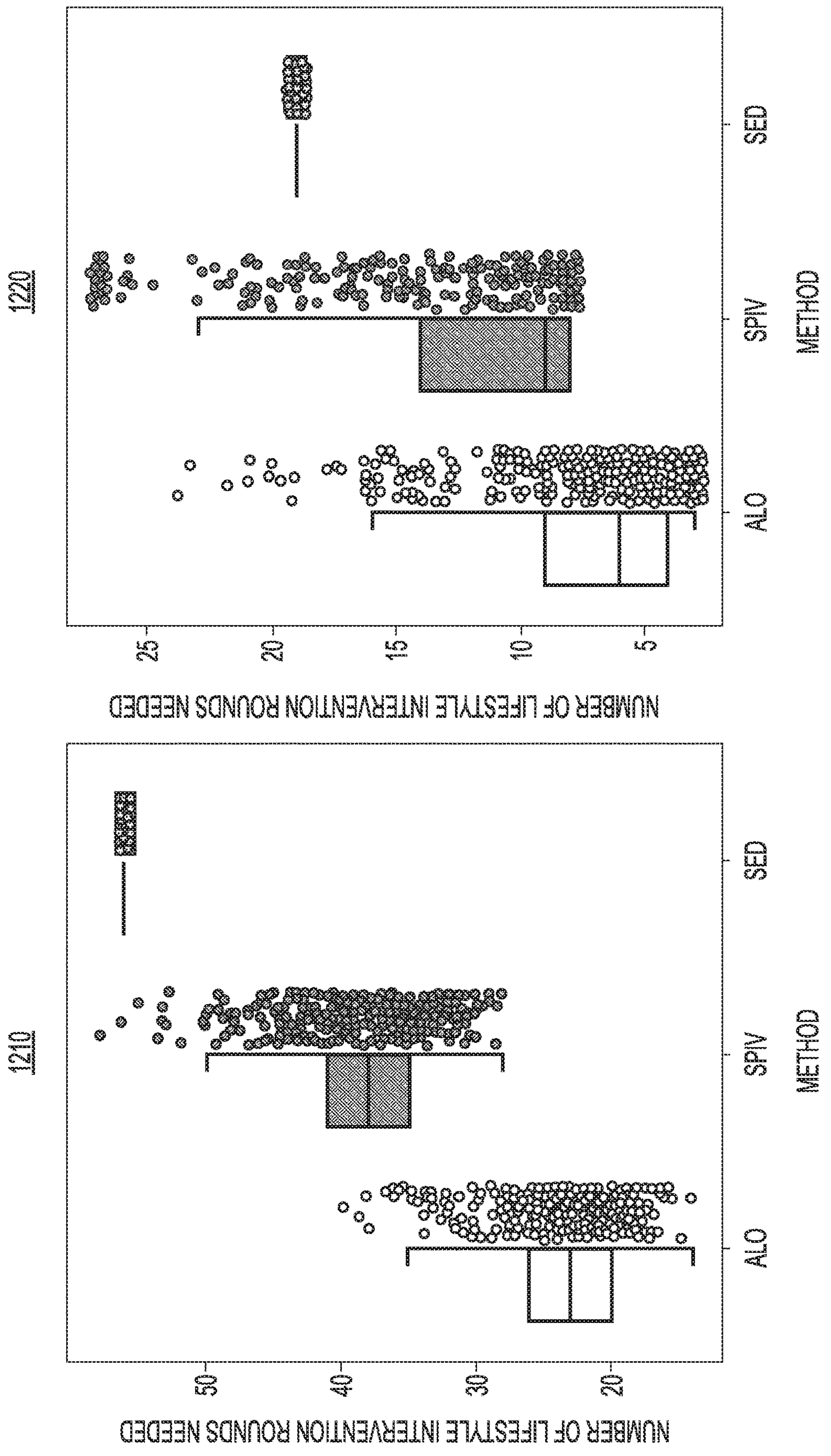
FIG. 12 depicts exemplary results related to IBS food intolerances and allergy identification, in accordance with various embodiments.

According to some embodiments, IBS is a known chronic gastrointestinal disease with 11% prevalence in adults. One of the most effective symptom management strategies of IBS is to identify their food intolerances (i.e., food items that exacerbate IBS symptoms such as bloating, constipation, diarrhea, and abdominal pain) and eliminate them from the patient's diet. By some embodiments, there is used ALO for discovery of food intolerances based on realistic synthetic data of 500 IBS patients given self-reported intolerance statistics of 56 food items and compared the performance of ALO with the standard elimination diet (SED) involving a constant 56 of LI rounds. FIG. 12 depicts exemplary results related to IBS food intolerance and allergy identification. Referring to FIG. 12, graph 1210 depicts that ALO and SPIV methods lead into 58.9% and 32.1% reduction in median number of lifestyle intervention (LI) rounds needed as compared to SED, for discovering the foods that exacerbate IBS symptoms amongst 56 foods in 500 IBS patients. Further, referring to graph 1220 of FIG. 12, it is seen that the median number of LI rounds needed compared to SED was reduced by 68.4% using ALO, and by 52.6% using SPIV, for identifying the foods that trigger food allergies in 500 patients. In other words, the evaluation results of FIG. 12 indicate that ALO reduced the median number of LI rounds by 68.4% (13/19), while the SPIV method resulted in 52.6% (10/19) reduction compared to SED. Both ALO and SPIV show considerable performance advantages over SED, while ALO method was 15.8% more efficient than SPIV.

Computer System

Figure 13:
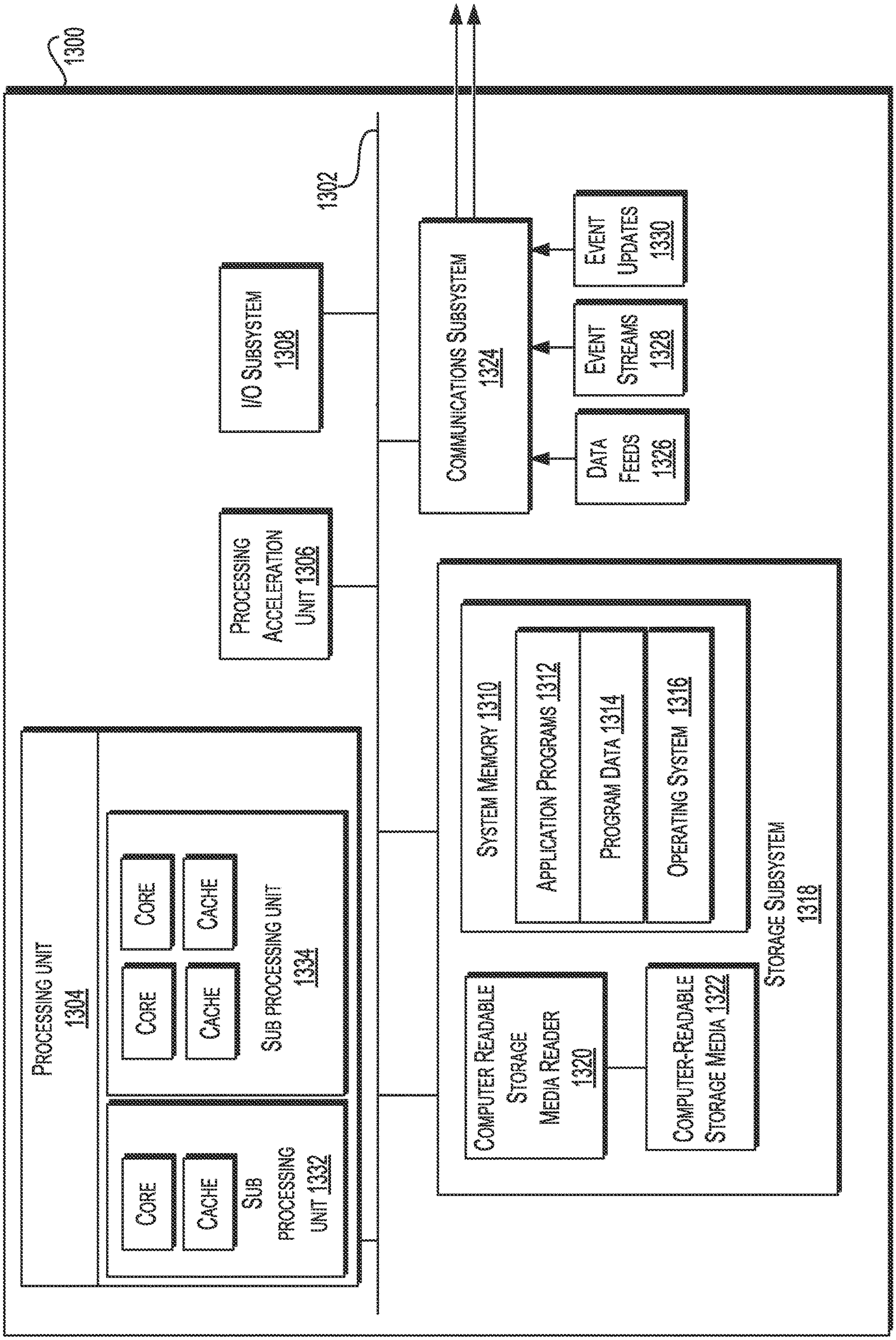
FIG. 13 is a block diagram illustrating an example computer system, according to at least one embodiment.

FIG. 13 illustrates an example computer system 1300, in which various embodiments may be implemented. The system 1300 may be used to implement any of the computer systems described above. As shown in the figure, computer system 1300 includes a processing unit 1304 that communicates with a number of peripheral subsystems via a bus subsystem 1302. These peripheral subsystems may include a processing acceleration unit 1306, an I/O subsystem 1308, a storage subsystem 1318 and a communications subsystem 1324. Storage subsystem 1318 includes tangible computer-readable storage media 1322 and a system memory 1310.

Bus subsystem 1302 provides a mechanism for letting the various components and subsystems of computer system 1300 communicate with each other as intended. Although bus subsystem 1302 is shown schematically as a single bus, alternative embodiments of the bus subsystem may utilize multiple buses. Bus subsystem 1302 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 1304, which can be implemented as one or more integrated circuits (e.g., a conventional microprocessor or microcontroller), controls the operation of computer system 1300. One or more processors may be included in processing unit 1304. These processors may include single core or multicore processors. In certain embodiments, processing unit 1304 may be implemented as one or more independent processing units 1332 and/or 1334 with single or multicore processors included in each processing unit. In other embodiments, processing unit 1304 may also be implemented as a quad-core processing unit formed by integrating two dual-core processors into a single chip.

In various embodiments, processing unit 1304 can execute a variety of programs in response to program code and can maintain multiple concurrently executing programs or processes. At any given time, some or all of the program code to be executed can be resident in processor(s) 1304 and/or in storage subsystem 1318. Through suitable programming, processor(s) 1304 can provide various functionalities described above. Computer system 1300 may additionally include a processing acceleration unit 1306, which can include a digital signal processor (DSP), a special-purpose processor, and/or the like.

I/O subsystem 1308 may include user interface input devices and user interface output devices. User interface input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may include, for example, motion sensing and/or gesture recognition devices such as the Microsoft Kinect® motion sensor that enables users to control and interact with an input device, such as the Microsoft Xbox® 360 game controller, through a natural user interface using gestures and spoken commands. User interface input devices may also include eye gesture recognition devices such as the Google Glass® blink detector that detects eye activity (e.g., 'blinking' while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

User interface input devices may also include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computer system 1300 to a user or other computer. For example, user interface output devices may include, without limitation, a variety of display devices that visually convey text, graphics and audio/video information such as monitors, printers, speakers, headphones, automotive navigation systems, plotters, voice output devices, and modems.

Computer system 1300 may comprise a storage subsystem 1318 that comprises software elements, shown as being currently located within a system memory 1310. System memory 1310 may store program instructions that are loadable and executable on processing unit 1304, as well as data generated during the execution of these programs.

Depending on the configuration and type of computer system 1300, system memory 1310 may be volatile (such as random-access memory (RAM)) and/or non-volatile (such as read-only memory (ROM), flash memory, etc.) The RAM typically contains data and/or program modules that are immediately accessible to and/or presently being operated and executed by processing unit 1304. In some implementations, system memory 1310 may include multiple different types of memory, such as static random-access memory (SRAM) or dynamic random-access memory (DRAM). In some implementations, a basic input/output system (BIOS), containing the basic routines that help to transfer information between elements within computer system 1300, such as during start-up, may typically be stored in the ROM. By way of example, and not limitation, system memory 1310 also illustrates application programs 1312, which may include client applications, Web browsers, mid-tier applications, relational database management systems (RDBMS), etc., program data 1314, and an operating system 1316. By way of example, operating system 1316 may include various versions of Microsoft Windows®, Apple Macintosh®, and/or Linux operating systems, a variety of commercially available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® 10 OS, and Palm® OS operating systems.

Storage subsystem 1318 may also provide a tangible computer-readable storage medium for storing the basic programming and data constructs that provide the functionality of some embodiments. Software (programs, code modules, instructions) that when executed by a processor provide the functionality described above may be stored in storage subsystem 1318. These software modules or instructions may be executed by processing unit 1304. Storage subsystem 1318 may also provide a repository for storing data used in accordance with the present disclosure.

Storage subsystem 1300 may also include a computer-readable storage media reader 1320 that can further be connected to computer-readable storage media 1322. Together and optionally, in combination with system memory 1310, computer-readable storage media 1322 may comprehensively represent remote, local, fixed, and/or removable storage devices plus storage media for temporarily and/or more permanently containing, storing, transmitting, and retrieving computer-readable information.

Computer-readable storage media 1322 containing code, or portions of code, can also include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information, and which can be accessed by computing system 1300.

By way of example, computer-readable storage media 1322 may include a hard disk drive that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD ROM, DVD, and Blu-Ray® disk, or other optical media. Computer-readable storage media 1322 may include, but is not limited to, Zip® drives, flash memory cards, universal serial bus (USB) flash drives, secure digital (SD) cards, DVD disks, digital video tape, and the like. Computer-readable storage media 1322 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magneto-resistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 1300.

Communications subsystem 1324 provides an interface to other computer systems and networks. Communications subsystem 1324 serves as an interface for receiving data from and transmitting data to other systems from computer system 1300. For example, communications subsystem 1324 may enable computer system 1300 to connect to one or more devices via the Internet. In some embodiments communications subsystem 1324 can include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components. In some embodiments communications subsystem 1324 can provide wired network connectivity (e.g., Ethernet) in addition to or instead of a wireless interface.

In some embodiments, communications subsystem 1324 may also receive input communication in the form of structured and/or unstructured data feeds 1326, event streams 1328, event updates 1330, and the like on behalf of one or more users who may use computer system 1300.

By way of example, communications subsystem 1324 may be configured to receive data feeds 1326 in real-time from users of social networks and/or other communication services such as Twitter® feeds, Facebook® updates, web feeds such as Rich Site Summary (RSS) feeds, and/or real-time updates from one or more third party information sources.

Additionally, communications subsystem 1324 may also be configured to receive data in the form of continuous data streams, which may include event streams 1328 of real-time events and/or event updates 1330, that may be continuous or unbounded in nature with no explicit end. Examples of applications that generate continuous data may include, for example, sensor data applications, financial tickers, network performance measuring tools (e.g., network monitoring and traffic management applications), clickstream analysis tools, automobile traffic monitoring, and the like.

Communications subsystem 1324 may also be configured to output the structured and/or unstructured data feeds 1326, event streams 1328, event updates 1330, and the like to one or more databases that may be in communication with one or more streaming data source computers coupled to computer system 1300.

Computer system 1300 can be one of various types, including a handheld portable device (e.g., an iPhone® cellular phone, an iPad® computing tablet, a PDA), a wearable device (e.g., a Google Glass® head mounted display), a PC, a workstation, a mainframe, a kiosk, a server rack, or any other data processing system.

Due to the ever-changing nature of computers and networks, the description of computer system 1300 depicted in the figure is intended only as a specific example. Many other configurations having more or fewer components than the system depicted in the figure are possible. For example, customized hardware might also be used and/or particular elements might be implemented in hardware, firmware, software (including applets), or a combination. Further, connection to other computing devices, such as network input/output devices, may be employed. Based on the disclosure and teachings provided herein, a person of ordinary skill in the art will appreciate other ways and/or methods to implement the various embodiments.

Although specific embodiments have been described, various modifications, alterations, alternative constructions, and equivalents are also encompassed within the scope of the disclosure. Embodiments are not restricted to operation within certain specific data processing environments but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A method for group testing a set of lifestyle interventions, the method comprising:

initializing, by a server, a model with respect to a set of lifestyle interventions received from a device associated with a user, the initializing including: (i) encoding the model as a tree including a plurality of nodes, wherein each node of the tree is representative of a list of lifestyle interventions and includes metadata information associated with the node, and (ii) assigning the set of lifestyle interventions received from the device to the list of lifestyle interventions associated with a root node of the tree;

for each node of the tree, identifying, a first subset of the list of lifestyle interventions associated with the node to be assigned to a first child node of the node, and a second subset of the list of lifestyle interventions associated with the node to be assigned to a second child node of the node;

selecting one of the first child node and the second child node to be utilized for a next round of processing based on an evaluation of each of the first child node and the second child node, updating metadata information associated with the first child node and the second child node based on the evaluation;

wherein the server, for each node, accesses a catalog of precomputed group testing parameters to determine an optimal group size and number of rounds for partitioning the set of lifestyle interventions, and, in response to user-specific feedback, revises a structure of the tree and associated metadata by splitting a node into child nodes and updating metadata information for the node and child nodes; and iteratively repeating the identifying, the selecting, and the updating until a stopping criterion is satisfied; and transmitting metadata information to the device associated with the user, wherein the metadata information includes a potency computed by the server for each lifestyle intervention in the set of lifestyle interventions, the potency for each lifestyle intervention being rendered in a user interface of an application executing on the device associated with the user, and enabling a selection, via the user interface, of one or more lifestyle interventions from the set of lifestyle interventions for achieving a target outcome.

2. The method of claim 1, wherein metadata information associated with each node includes:

a first set ($V_0$) including lifestyle interventions from the set of lifestyle interventions that have been determined as being impotent, a second set ($V_1$) including lifestyle interventions from the set of lifestyle interventions that have been determined as being potent, a first parameter n corresponding to a number of lifestyle interventions included in the list of lifestyle interventions associated with the node, a second parameter l corresponding to a minimum number of potent lifestyle interventions included in the list of lifestyle interventions associated with the node, and a third parameter h corresponding to a maximum number of potent lifestyle interventions included in the list of lifestyle interventions associated with the node.

3. The method of claim 2, wherein the step of initializing the model further comprises:

setting, each of the first set ($V_0$) and the second set ($V_1$) associated with the root node of the tree to a null set; and estimating by the server, the third parameter h associated with the root node.

4. The method of claim 3, wherein the third parameter h associated with the root node is estimated based on a confidence threshold parameter, and a probability distribution of potency probabilities of the set of lifestyle interventions.

5. The method of claim 1, wherein a number of lifestyle interventions included in the first subset of the list of lifestyle interventions is determined based on a catalog generated with respect to the set of lifestyle interventions received from a device, the number of lifestyle interventions being selected from the list of lifestyle interventions in a random fashion.

6. The method of claim 1, further comprising:
generating, by the server, a catalog including data associated with the set of lifestyle interventions received from the device associated with the user, wherein the data includes a plurality of records, each record including a mapping of a 3-tuple including parameters n, l, and h, to a 2-tuple including parameters s and w, wherein
n corresponds to a number of lifestyle interventions,
l corresponds to a minimum number of potent lifestyle interventions,
h corresponds to a maximum number of potent lifestyle interventions,
s corresponds to an optimal count of lifestyle interventions to be considered for execution of the model, and
w corresponds to a maximum number of executions of the model that is required to obtain potencies of n lifestyle interventions.

7. The method of claim 1, wherein the first subset of the list of lifestyle interventions assigned to the first child node is disjoint with respect to the second subset of the list of lifestyle interventions assigned to the second child node.

8. The method of claim 1, wherein the evaluation of each of the first child node and the second child node comprises:
simulating the model for a first potency response value of the first subset;
simulating the model for a second potency response value of the first subset;
identifying, based on a catalog generated with respect to the set of lifestyle interventions, a first result of simulating the model for the first potency response value of the first subset, and a second result of simulating the model for the second potency response value of the first subset, a first maximum number of rounds of model execution required to determining potencies of lifestyle interventions included in the first subset;
simulating the model for the first potency response value of the second subset;
simulating the model for the second potency response value of the second subset;
identifying, based on the catalog, a third result of simulating the model for the first potency response value of the second subset, and a fourth result of simulating the model for the second potency response value of the second subset, a second maximum number of rounds of model execution required to determining potencies of lifestyle interventions included in the second subset; and
selecting one of the first child node and the second child node based on a comparison of the first maximum number of rounds of model execution with respect to the second maximum number of rounds of model execution.

9. The method of claim 8, further comprising:
selecting the first child node in response to the first maximum number of rounds of model execution being lower than the second maximum number of rounds of model execution.

10. The method of claim 8, further comprising:
selecting the second child node in response to the second maximum number of rounds of model execution being lower than the first maximum number of rounds of model execution.

11. The method of claim 1, wherein the stopping criterion corresponds to a potency of each lifestyle intervention included in the set of lifestyle interventions being determined as one of potent or impotent.

12. The method of claim 1, wherein the tree is a binary tree.

13. A server for group testing a set of lifestyle interventions, the server comprising:
a processor; and
a memory including instructions that, when executed with the processor, cause the server to, at least:
initialize a model with respect to a set of lifestyle interventions received from a device associated with a user, wherein initializing the model includes: (i) encoding the model as a tree including a plurality of nodes, wherein each node of the tree is representative of a list of lifestyle interventions and includes metadata information associated with the node, and (ii) assigning the set of lifestyle interventions received from the device to the list of lifestyle interventions associated with a root node of the tree;
for each node of the tree,
(a) identify, a first subset of the list of lifestyle interventions associated with the node to be assigned to a first child node of the node, and a second subset of the list of lifestyle interventions associated with the node to be assigned to a second child node of the node;
(b) select one of the first child node and the second child node to be utilized for a next round of processing based on an evaluation of each of the first child node and the second child node,
(c) update metadata information associated with the first child node and the second child node based on the evaluation, wherein the server, for each node, accesses a catalog of precomputed group testing parameters to determine an optimal group size and number of rounds for partitioning the set of lifestyle interventions, and, in response to user-specific feedback, revises a structure of the tree and associated metadata by splitting a node into child nodes and updating metadata information for the node and child nodes; and
(d) iteratively repeat (a)-(c) until a stopping criterion is satisfied; and
transmit metadata information to the device associated with the user, wherein the metadata information includes a potency computed by the server for each lifestyle intervention in the set of lifestyle interventions, the potency for each lifestyle intervention being rendered in a user interface of an application executing on the device associated with the user, and enabling a selection, via the user interface, of one or more lifestyle interventions from the set of lifestyle interventions for achieving a target outcome.

14. The server of claim 13, wherein metadata information associated with each node includes:
a first set ($V_0$) including lifestyle interventions from the set of lifestyle interventions that have been determined as being impotent,
a second set ($V_1$) including lifestyle interventions from the set of lifestyle interventions that have been determined as being potent, a first parameter n corresponding to a number of lifestyle interventions included in the list of lifestyle interventions associated with the node, a second parameter l corresponding to a minimum number of potent lifestyle interventions included in the list of lifestyle interventions associated with the node, and a third parameter h corresponding to a maximum number of potent lifestyle interventions included in the list of lifestyle interventions associated with the node.

15. The server of claim 14, wherein the processor is further configured to:

set, each of the first set ($V_0$) and the second set ($V_1$) associated with the root node of the tree to a null set; and estimate, the third parameter h associated with the root node.

16. The server of claim 15, wherein the third parameter h associated with the root node is estimated based on a confidence threshold parameter, and a probability distribution of potency probabilities of the set of lifestyle interventions.

17. The server of claim 13, wherein a number of lifestyle interventions included in the first subset of the list of lifestyle interventions is determined based on a catalog generated with respect to the set of lifestyle interventions received from a device, the number of lifestyle interventions being selected from the list of lifestyle interventions in a random fashion.

18. The server of claim 13, wherein the first subset of the list of lifestyle interventions assigned to the first child node is disjoint with respect to the second subset of the list of lifestyle interventions assigned to the second child node.

19. The server of claim 13, wherein the processor is further configured to evaluate each of the first child node and the second child node by:

simulate the model for a first potency response value of the first subset;

simulate the model for a second potency response value of the first subset;

identify, based on a catalog generated with respect to the set of lifestyle interventions, a first result of simulating the model for the first potency response value of the first subset, and a second result of simulating the model for the second potency response value of the first subset, a first maximum number of rounds of model execution required to determining potencies of lifestyle interventions included in the first subset;

simulate the model for the first potency response value of the second subset;

simulate the model for the second potency response value of the second subset;

identify, based on the catalog, a third result of simulating the model for the first potency response value of the second subset, and a fourth result of simulating the model for the second potency response value of the second subset, a second maximum number of rounds of model execution required to determining potencies of lifestyle interventions included in the second subset; and select one of the first child node and the second child node based on a comparison of the first maximum number of rounds of model execution with respect to the second maximum number of rounds of model execution.

20. A non-transitory computer readable medium storing specific computer-executable instructions that, when executed by a processor, cause a computer system for performing group testing of a set of lifestyle interventions, the computer system configured to at least:

initializing, by a server, a model with respect to a set of lifestyle interventions received from a device associated with a user, the initializing including: (i) encoding the model as a tree including a plurality of nodes, wherein each node of the tree is representative of a list of lifestyle interventions and includes metadata information associated with the node, and (ii) assigning the set of lifestyle interventions received from the device to the list of lifestyle interventions associated with a root node of the tree;

for each node of the tree, identifying, a first subset of the list of lifestyle interventions associated with the node to be assigned to a first child node of the node, and a second subset of the list of lifestyle interventions associated with the node to be assigned to a second child node of the node;

selecting one of the first child node and the second child node to be utilized for a next round of processing based on an evaluation of each of the first child node and the second child node, updating metadata information associated with the first child node and the second child node based on the evaluation;

wherein the server, for each node, accesses a catalog of precomputed group testing parameters to determine an optimal group size and number of rounds for partitioning the set of lifestyle interventions, and, in response to user-specific feedback, revises a structure of the tree and associated metadata by splitting a node into child nodes and updating metadata information for the node and child nodes; and iteratively repeating the identifying, the selecting, and the updating until a stopping criterion is satisfied; and transmitting metadata information to the device associated with the user, wherein the metadata information includes a potency computed by the server for each lifestyle intervention in the set of lifestyle interventions, the potency for each lifestyle intervention being rendered in a user interface of an application executing on the device associated with the user, and enabling a selection, via the user interface, of one or more lifestyle interventions from the set of lifestyle interventions for achieving a target outcome.

* * * * *